United States Patent
Xiao et al.

(10) Patent No.: US 8,153,630 B2
(45) Date of Patent: Apr. 10, 2012

(54) KINASE INHIBITORS

(75) Inventors: Xiao-Yi Xiao, San Diego, CA (US);
Dinesh V. Patel, Fremont, CA (US)

(73) Assignee: Miikana Therapeutics, Inc., Rockville, MD (US)

( * ) Notice: Subject to any disclaimer, the term of this patent is extended or adjusted under 35 U.S.C. 154(b) by 1066 days.

(21) Appl. No.: 11/667,205

(22) PCT Filed: Nov. 17, 2005

(86) PCT No.: PCT/US2005/041945
§ 371 (c)(1),
(2), (4) Date: Nov. 23, 2007

(87) PCT Pub. No.: WO2006/055831
PCT Pub. Date: May 26, 2006

(65) Prior Publication Data
US 2008/0200485 A1 Aug. 21, 2008

Related U.S. Application Data

(60) Provisional application No. 60/629,176, filed on Nov. 17, 2004.

(51) Int. Cl.
*C07D 403/12* (2006.01)
*C07D 239/553* (2006.01)
*A61K 31/4155* (2006.01)

(52) U.S. Cl. .................. 514/235.8; 514/274; 544/122; 544/317

(58) Field of Classification Search .................. 544/122, 544/317; 514/235.8, 274
See application file for complete search history.

(56) References Cited

U.S. PATENT DOCUMENTS

| | | | |
|---|---|---|---|
| 4,450,162 A | 5/1984 | Kamioka et al. |
| 5,453,414 A | 9/1995 | Tice et al. |
| 5,525,604 A | 6/1996 | Lee et al. |
| 5,852,023 A | 12/1998 | Schaper et al. |
| 5,916,908 A | 6/1999 | Giese et al. |
| 6,200,977 B1 | 3/2001 | Cushing et al. |
| 6,207,401 B1 | 3/2001 | Plowman et al. |
| 6,432,947 B1 | 8/2002 | Arnaiz et al. |
| 6,462,069 B2 | 10/2002 | Reich et al. |
| 6,528,513 B2 | 3/2003 | Cushing et al. |
| 6,610,677 B2 | 8/2003 | Davies et al. |
| 6,613,776 B2 | 9/2003 | Knegtel et al. |
| 6,638,926 B2 | 10/2003 | Davies et al. |
| 6,642,227 B2 | 11/2003 | Cao et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,660,731 B2 | 12/2003 | Bebbington et al. |
| 6,664,247 B2 | 12/2003 | Bebbington et al. |
| 6,677,337 B2 | 1/2004 | Laufersweiler et al. |
| 6,696,452 B2 | 2/2004 | Davies et al. |
| 6,727,251 B2 | 4/2004 | Bebbington et al. |
| 6,762,179 B2 | 7/2004 | Cochran et al. |
| 6,784,195 B2 | 8/2004 | Hale et al. |
| 6,825,190 B2 | 11/2004 | Moon et al. |
| 6,835,726 B2 | 12/2004 | Cushing et al. |
| 6,838,464 B2 | 1/2005 | Pease et al. |
| 6,841,579 B1 | 1/2005 | Plowman et al. |
| 6,846,928 B2 | 1/2005 | Bebbington et al. |
| 6,875,789 B2 | 4/2005 | Tang et al. |
| 6,989,385 B2 | 1/2006 | Bebbington et al. |

(Continued)

FOREIGN PATENT DOCUMENTS

JP 6-65237 3/1994

(Continued)

OTHER PUBLICATIONS

Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*
Banker et al., Prodrugs, Modern Pharmaceutics, Third Edition and Expanded, pp. 451 and 596.*
Simone, Oncology: Introduction, Cecil Textbook of Medicine, 20th Edition, vol. 1, pp. 1004-1010, 1996.*

(Continued)

*Primary Examiner* — Deepak Rao
(74) *Attorney, Agent, or Firm* — Johnson, Marcou & Isaacs, LLC; Robert E. Richards

(57) ABSTRACT

Disclosed are protein kinase inhibitors of Formula Ia and Ib, compositions comprising such inhibitors, and methods of use, thereof. More particularly, these compounds and compositions are inhibitors of Aurora-A (Aurora-2) and Aurora-B (Aurora-1) protein kinase. Also disclosed are methods of using these compounds and compositions to prevent and treat diseases associated with protein kinases, especially diseases associated with Aurora-A or Aurora-B, such as cancer.

12 Claims, No Drawings

U.S. PATENT DOCUMENTS

| | | | |
|---|---|---|---|
| 6,995,159 B2 | 2/2006 | Chiang et al. |
| 7,008,948 B2 | 3/2006 | Bebbington et al. |
| 7,067,522 B2 | 6/2006 | Pease et al. |
| 7,084,159 B2 | 8/2006 | Cao et al. |
| 7,087,603 B2 | 8/2006 | Bebbington et al. |
| 7,091,343 B2 | 8/2006 | Bebbington et al. |
| 7,098,330 B2 | 8/2006 | Bebbington et al. |
| 7,115,597 B2 | 10/2006 | Bilodeau et al. |
| 7,115,739 B2 | 10/2006 | Bebbington et al. |
| 7,179,826 B2 | 2/2007 | Bebbington et al. |
| 7,226,923 B2 | 6/2007 | Boyd et al. |
| 7,244,735 B2 | 7/2007 | Straub et al. |
| 2001/0018436 A1 | 8/2001 | Cushing et al. |
| 2002/0052386 A1 | 5/2002 | Armistead et al. |
| 2002/0065270 A1 | 5/2002 | Moriarty et al. |
| 2002/0137755 A1 | 9/2002 | Bilodeau et al. |
| 2003/0055068 A1 | 3/2003 | Bebbington et al. |
| 2003/0064982 A1 | 4/2003 | Davies et al. |
| 2003/0069239 A1 | 4/2003 | Cai et al. |
| 2003/0096816 A1 | 5/2003 | Cao et al. |
| 2003/0105090 A1 | 6/2003 | Bebbington et al. |
| 2003/0144309 A1 | 7/2003 | Choon-Moon |
| 2003/0207873 A1 | 11/2003 | Harrington |
| 2004/0006068 A1 | 1/2004 | Cushing et al. |
| 2004/0009981 A1 | 1/2004 | Bebbington et al. |
| 2004/0023963 A1 | 2/2004 | Cao et al. |
| 2004/0023977 A1 | 2/2004 | Larsen et al. |
| 2004/0049032 A1 | 3/2004 | Charrier et al. |
| 2004/0087789 A1 | 5/2004 | Beauchamp et al. |
| 2004/0097531 A1 | 5/2004 | Ledeboer et al. |
| 2004/0116454 A1 | 6/2004 | Davies |
| 2004/0157893 A1 | 8/2004 | Bebbington et al. |
| 2004/0167141 A1 | 8/2004 | Bebbington et al. |
| 2004/0214814 A1 | 10/2004 | Bebbington et al. |
| 2005/0038023 A1 | 2/2005 | Bebbington et al. |
| 2005/0070561 A1 | 3/2005 | Jung et al. |
| 2005/0113382 A1 | 5/2005 | Jahangir et al. |
| 2005/0192294 A1 | 9/2005 | Rudolph et al. |
| 2006/0004030 A1 | 1/2006 | Ebden et al. |
| 2006/0084650 A1 | 4/2006 | Dong et al. |
| 2006/0106029 A1 | 5/2006 | Ohkubo et al. |
| 2006/0135541 A1 | 6/2006 | Mortlock et al. |
| 2006/0142572 A1 | 6/2006 | Martinez-Botella et al. |
| 2006/0258658 A1 | 11/2006 | Bebbington et al. |
| 2006/0270660 A1 | 11/2006 | Charrier et al. |
| 2007/0037888 A1 | 2/2007 | Nowak et al. |
| 2007/0270444 A1 | 11/2007 | Bebbington et al. |
| 2008/0200485 A1 | 8/2008 | Xiao et al. |

FOREIGN PATENT DOCUMENTS

| | | | |
|---|---|---|---|
| WO | WO 00/21955 A1 | 4/2000 |
| WO | WO 00/39101 A1 | 7/2000 |
| WO | WO 02/18346 A1 | 3/2002 |
| WO | WO 02/22601 A1 | 3/2002 |
| WO | WO 02/22606 | 3/2002 |
| WO | WO 02/24667 A1 | 3/2002 |
| WO | WO 02/50065 | 6/2002 |
| WO | WO 02/057259 | 7/2002 |
| WO | WO 02/059111 | 8/2002 |
| WO | WO 02/062789 | 8/2002 |
| WO | WO 02/066461 | 8/2002 |
| WO | WO 02/068415 A1 | 9/2002 |
| WO | WO 03/092607 A2 | 11/2003 |
| WO | WO 2004/037814 A1 | 5/2004 |
| WO | WO 2006/055831 | 5/2006 |

OTHER PUBLICATIONS

Rogers et al., PubMed Abstract (J Cell Biol. 157(2):219-29, Epub) Apr. 2002.*

Tanaka et al., PubMed Abstract (Cell 108(3):317-29) Feb. 2002.*

Gura, Systems for identifying New Drugs Are Often Faulty, Cancer Models, Science, vol. 278, No. 5340, pp. 1041-1042, Nov. 1997.*

Johnson et al., Relationships between drug activity in NCI preclinical in vitro and in vivo models and early clinical trials, British Journal of Cancer (2001) 64(10): 1424-1431.*

Caravajal et al., Aurora Kinases: New Targets for Cancer Therapy, Clin Cancer Res 2006:12(23), pp. 6869-6875, Dec. 1, 2006.*

Silverman, Prodrugs and Drug Delivery Systems, The Organic Chemistry of Drug Design and Drug Action, pp. 352-399, 1992.*

International Search Report and Written Opinion for PCT/US05/41945, PCT Search Report and Written Opinion, pp. 1-7, May 16, 2006.

Ukrainian Patent Office Action—Appl. No. 200805165/with English Translation, pp. 1-4, Nov. 10, 2010.

Chinese Office Action—Appl. No. 200680044656.7, pp. 1-10, May 12, 2010.

EPO Search Report cited in EP Application No. 05851859.8, pp. 1-8, Jun. 10, 2009.

EPO Search Report cited in EP Application No. 05851859.8, pp. 1-4, Sep. 21, 2010.

EPO Search Report cited in EP Application No. 08768344.7, pp. 1-5, Aug. 31, 2010.

New Zealand Patent Examination Report—Appl. No. 567241, pp. 1-2, Jan. 21, 2010.

Chinese Office Action—Application No. 200580044086.7, pp. 1-10, Aug. 5, 2009.

Medicaments—A Handbook for Physicians with English translation, pp. 1-5, Jan. 1, 2001.

Singapore Notification with Australian Written Opinion—Appl. No. SG 200802418-4, pp. 1-4, Apr. 8, 2009.

Russian Official Action with English Translation—Appl. No. 2008117104/04, pp. 1-13, Jun. 23, 2010.

Russian Official Action—Appl. No. 2007122485/04, pp. 1-5, Sep. 30, 2009.

Australian Patent Exam Report—Appl. No. 2005306458, pp. 1-2, Oct. 27, 2010.

Indonesian Exam Report—ID Application No. W00 2008 00989, pp. 1-2, Jun. 21, 2010.

U.S. Appl. No. 11/541,484 mailed Dec. 31, 2008, USPTO Office Action, pp. 1-5, Dec. 31, 2008.

Singapore Notification with Australian Exam. Report—Appl. No. SG 200703562-9, Australian Written Opinion for Singapore, pp. 1-7, Jul. 14, 2008.

Taylor et al., 1-Alkylcarbonyloxymethyl Prodrugs of 5-Fluorouracil (5-FU): Synthesis, Physicochemical Properties, and Topical Delivery of 5-FU, Journal of Pharmaceutical Sciences, vol. 87 (1), pp. 1-7, Oct. 17, 1997.

Singapore Notification with Australian Exam. Report—Appl. No. SG 200802418-4, pp. 1-6, Nov. 23, 2009.

International Search Report and Written Opinion for PCT/US09/65496, pp. 1-8, Feb. 2, 2010.

International Search Report and Written Opinion for PCT/US06/38174, pp. 1-10, Jul. 20, 2007.

Fry et al., Inhibitors of Cyclin-Dependent Kinases as Therapeutic Agents for the Treatment of Cancer, Current Opinion in Oncologic, Endocrine and Metabolic Investigational Drugs, vol. 2 (1), pp. 40-59, Jan. 1, 2000.

Sausville, E., Aurora Kinases Dawn as Cancer Drug Targets, Nature Medicine, vol. 10 (3), pp. 234-267, Mar. 1, 2004.

Cheetham et al., Crystal Structure of Aurora-2, an Oncogenic Serine/Threonine Kinase, The Journal of Biological Chemistry, vol. 277, Nov. 8, 2002.

EPO Search Report cited in EP Application No. 0581859.8, pp. 1-7, Jun. 10, 2009.

International Search Report and Written Opinion for PCT/US08/07288, pp. 1-9, Sep. 12, 2008.

Anderson et al., Requirement for Integration of Signals from Two Distinct Phophorylation Pathways for Activiation of MAP Kinase, Nature, vol. 343, pp. 641-653, Feb. 15, 1990.

Andrews et al., Mitotic Mechanics: The Auroras Come Into View Current Opinion in Cell Biology, vol. 15, pp. 672-683, Jan. 1, 2003.

Biscardi et al., c-Src, Receptor Tyrosine Kinases, and Human Cancer, Advances in Cancer Research, vol. 76, pp. 61-119, Jan. 1, 1999.

Bjorbaek et al., Divergent Functional Roles for $p90^{rsk}$ Kinase Domains, The Journal of Biological Chemistry, vol. 270(32), pp. 18848-18852, Jan. 1, 1995.

Bokemeyer et al., Multiple Intracellular MAP Kinase Signaling Cascades, Kidney International, vol. 49, pp. 1187-1198, May 1, 1996.

Bolen et al., Activation of pp60$^{c-src}$ Protein Kinase Activity in Human Colon Carcinoma, *Proceedings of the National Academy of Sciences USA*, vol. 84, pp. 2251-2255, Apr. 1, 1987.

Boschelli et al., Small Molecule Inhibitors of Src Family Kinases, *Drugs of the Future*, vol. 25 (7), pp. 717-736, Jan. 1, 2000.

Brown et al., Evolutionary Relationships of Aurora Kinases: Implications for Model Organism Studies and the Development of Anti-Cancer Drugs, *BMC Evolutionary Biology*, vol. 4 (39), pp. 1-10, Jan. 1, 2004.

Carmena et al., The Cellular Geography of Aurora Kinases, *Nature*, vol. 4, pp. 842-854, Nov. 1, 2003.

Castro et al., Involvement of Aurora A Kinase During Meiosis I-II Transition in *Xenopus* Oocytes, *The Journal of Biological Chemistry*, vol. 278 (4), pp. 2236-2241, Jan. 1, 2003.

Cheetham et al., Crystal Structure of Aurora-2, an Oncogenic Serine/Threonine Kinase, *The Journal of Biological Chemistry*, vol. 277 (45), pp. 42419-42422, Nov. 8, 2002.

Chen et al., Phosphorylation of the c-Fos Transrepression Domain by Mitogen-Activated Protein Kinase and 90-kDa Ribosomal S6 Kinase, *Proceedings of the National Academy of Sciences USA*, vol. 90, pp. 10952-10956, Dec. 1, 1993.

Crews et al., The Primary Structure of MEK, A Protein Kinase that Phosphorylates the ERK Gene Product, *Science*, vol. 258, pp. 478-480, Oct. 16, 1992.

Ditchfield et al., Aurora B Couples Chromosome Alignment with Anaphase by Targeting BubR1, Mad2, and Cenp-E to Kinetochores, *The Journal of Cell Biology*, vol. 161 (2), pp. 267-680, Apr. 28, 2003.

Druker et al., Activity of a Specific Inhibitor of the BCR-ABL Tyrosine Kinase in the Blast Crisis of Chronic Myeloid Leukemia and Acute Lymphoblastic Leukemia with the Philadelphia Chromosome, *The New England Journal of Medicine*, vol. 344 (14), pp. 1038-1043, Apr. 5, 2001.

Ferrara et al., Vascular Endothelial Growth Factor: Basic Science and Clinical Progress, *Endocrine Reviews*, vol. 25 (4), pp. 581-511, Aug. 1, 2004.

Fischer et al., Inhibitors of Cyclin-Dependent Kinases as Anti-Cancer Therapeutics, *Current Medicinal Chemistry*, vol. 7, pp. 1213-1245, Jan. 1, 2000.

Frey et al., Involvement of Extracellular Signal-Regulated Kinase 2 and Stress-Activated Protein Kinase/Jun N-Terminal Kinase Activation by Transforming Growth Factor β in the Negative Growth Control of Breast Cancer Cells, *Cancer Research*, vol. 57, pp. 628-633, Feb. 15, 1997.

Gomtsyan et al., Design, Synthesis, and Structure—Activity Relationship of 6-Alkynylpyrimidines as Potent Adenosine Kinase Inhibitors, *Journal of Medicinal Chemistry*, vol. 45, pp. 3639-3648, Aug. 15, 2002.

Harrington et al., VX-680, A Potent and Selective Small-Molecule Inhibitor of the Aurora Kinases, Suppresses Tumor Growth in vivo and Addendum (dated Apr. 2007), *Nature Medicine*, vol. 10 (3), pp. 262-267, Mar. 1, 2004.

Hauf et al., The Small Molecule Hesperadin Reveals a Role for Aurora B in Correcting Kinetochore-Microtubule Attachment and in Maintaining the Spindle Assembly Checkpoint, *The Journal of Cell Biology*, vol. 161 (2), pp. 281-294, Apr. 28, 2003.

Heinrich et al., Inhibition of KIT Tyrosine Kinase Activity: A Novel Molecular Approach to the Treatment of KIT-Positive Malignancies, *Journal of Clinical Oncology*, vol. 20 (6), pp. 1692-1703, Mar. 15, 2002.

Khwaja et al., AKT is More Than Just Bad Kinase, *Nature*, vol. 401, pp. 33-34, Sep. 2, 1999.

Lutz et al., Overexpression and Activation of the Tyrosine Kinase Src in Human Pancreatic Carcinoma, *Biochemical and Biophysical Research Communications*, vol. 243, pp. 503-508, Jan. 1, 1998.

Lynch et al., Increased Expression of the src Proto-Oncogene in Hairy Cell Leukemia and a Subgroup of B-Cell Lymphomas, *Leukemia*, vol. 7 (9), pp. 1416-1422, Sep. 1, 1993.

Mani et al., Cyclin-Dependent Kinase Inhibitors: Novel Anticancer Agents, *Expert Opinion on Investigational Drugs*, vol. 9 (8), pp. 1849-1870, Aug. 1, 2000.

Masaki et al., pp60$^{c-src}$ Activation in Hepatocellular Carcinoma of Humans and LEC Rats, *Hepatology*, vol. 27 (5), pp. 1257-1264, May 1, 1998.

Molina et al., Profound block in Thymocyte Development in Mice Lacking p56$^{kk}$, *Nature*, vol. 357, pp. 161-164, May 14, 1992.

Moodie et al., Complexes of Ras-GTP with Raf-1 and Mitogen-Activated Protein Kinase Kinase, *Science*, vol. 260, pp. 1658-1661, Jun. 11, 1993.

Namikawa et al., Akt/Protein Kinase B Prevents Injury-Induced Motoneuron Death and Accelerates Axonal Regeneration, *The Journal of Neuroscience*, vol. 20 (8), pp. 2875-2886, Apr. 15, 2000.

Oliver et al., Transforming Growth Factor-α and Epidermal Growth Factor Activate Mitogen-Activated Protein Kinase and Its Substrates in Intestinal Epithelial Cells, *Proceedings of the Society for Experimental Biology and Medicine*, vol. 210 (2), pp. 162-170, Nov. 1, 1995.

Raingeaud et al., MKK3- and MKK6-Regulated Gene Expression is Mediated by the p38 Mitogen-Activated Protein Kinase Signal Transduction Pathway, *Molecular and Cellular Biology*, vol. 16 (3), pp. 1247-1255, Mar. 1, 1996.

Rosen et al., Analysis of the pp60$^{c-src}$ Protein Kinase Activity in Human Tumor Cell Lines and Tissues, *The Journal of Biological Chemistry*, vol. 261 (29), pp. 13754-13759, Oct. 15, 1986.

Rouse et al., A Novel Kinase Cascade Triggered by Stress and Heat Shock that Stimulates MAPKAP Kinase-2 and Phosphorylation of the Small Heat Shock Proteins, *Cell*, vol. 78, pp. 1027-1037, Sep. 23, 1994.

Sakai et al., MBD3 and HDAC1, Two Components of the NuRD Complex, are Localized at Aurora-A-Positive Centrosomes in M Phase, *The Journal of Biological Chemistry*, vol. 277 (50), pp. 48714-48723, Dec. 13, 2002.

Scrittori et al., pEg2 Aurora-A Kinase, Histone H3 Phosphorylation, and Chromosome Assembly in *Xenopus* Egg Extract, *The Journal of Biological Chemistry*, vol. 276 (32), pp. 30002-30010, Aug. 10, 2001.

Sen et al., Amplification/Overexpression of a Mitotic Kinase Gene in Human Breast Cancer, *Journal of the National Cancer Institute*, vol. 94 (17), pp. 1320-1329, Sep. 4, 2002.

Silvaraman et al., Hyperexpression of Mitogen-Activated Protein Kinase in Human Breast Cancer, *Journal of Clinical Investigation*, vol. 99 (7), pp. 1478-1483, Apr. 1, 1997.

Soriano et al., Targeted Disruption of the c-src Proto-Oncogene Leads to Osteopetrosis in Mice, *Cell*, vol. 64, pp. 693-702, Feb. 22, 1991.

Staley et al., Decreased Tumorigenicity of a Human Colon Adenocarcinoma Cell Line by an Antisense Expression Vector Specific for c-Src$^1$, *Cell Growth & Differentiation*, vol. 8, pp. 269-274, Mar. 1, 1997.

Sternberg et al., Therapeutic Intervention in Leukemias that Express the Activated fms-like Tyrosine Kinase 3 (FLT3): Opportunities and Challenges, *Current Opinion in Hematology*, vol. 12, pp. 7-13, Jan. 1, 2004.

Takayanagi et al., Suppression of Arthritic Bone Destruction by Adenovirus-Mediated csk Gene Transfer to Synoviocytes and Osteoclasts, *The Journal of Clinical Investigation*, vol. 104 (2), pp. 137-146, Jul. 1, 1999.

Talamonti et al., Increase in Activity and Level of pp60$^{c-src}$ in Progressive Stages of Human Cancer, *Journal of Clinical Investigation*, vol. 91, pp. 53-60, Jan. 1, 1993.

Warner et al., Targeting Aurora-2 Kinase in Cancer, *Molecular Cancer Therapeutics*, vol. 2, pp. 589-595, Jun. 1, 2003.

Whelchel et al., Inhibition of ERK Activation Attenuates Endothelin-Stimulated Airway Smooth Muscle Cell Proliferation, *American Journal of Respiratory Cell and Molecular Biology*, vol. 16, pp. 589-596, Jan. 1, 1997.

Wiener et al., Decreased Src Tyrosine Kinase Activity Inhibits Malignant Human Ovarian Cancer Tumor Growth in a Nude Mouse Model, *Clinical Cancer Research*, vol. 5, pp. 2164-2170, Aug. 1, 1999.

Wong et al., Molecular Cloning and Nucleic Acid Binding Properties of the GAP-Associated Tyrosine Phosphoprotein p62, *Cell*, vol. 69, pp. 551-558, May 1, 1992.

Yuan et al., Frequent Activation of AKT2 and Induction of Apoptosis by Inhibition of Phosphoinositide-3-OH Kinase/Akt Pathway in Human Ovarian Cancer, *Oncogene*, vol. 19, pp. 2324-2330, Jan. 1, 2000.

Zhang et al., Aberrant Quantity and Localization of Aurora-B/AIM-1 and Survivin During Megakaryocyte Polyploidization and the Consequences of Aurora-B/AIM-1 Deregulated Expression, *Blood,* vol. 103 (10), pp. 3717-3726, May 15, 2004.

EPO Exam Report cited in EPO Application No. 08768344.7, pp. 1-4, Mar. 17, 2011.

EPO Examination Report issued in Appl. No. 05851859.8, pp. 1-4, Feb. 7, 2011.

Carvajal et al., Molecular Mechanism of cGMP-Mediated Smooth Muscle Relaxation, *Journal of Cellular Physiology,* vol. 184, pp. 409-420, Apr. 14, 2000.

Damasio, Antonio R., 400-Alzheimer's Disease and Related Dementias, *Cecil Textbook of Medicine,* vol. 20 Ed-2, pp. 1992-1996, Jan. 1, 1996.

Layzerm, Robert B., Section Five—Degenerative Diseases of the Nervous System, *Cecil Textbook of Medicine,* vol. 20th Ed-2, pp. 2050-2057, Jan. 1, 1996.

Office Action issued U.S. Appl. No. 12/137,355, USPTO Office Action, pp. 1-29, May 13, 2011.

Supplementary EPO Supplementary Search Report cited in Application No. EP 06825267.5, EPO Search Report, pp. 1-6, Dec. 17, 2010.

Office Action cited in U.S. Appl. No. 12/494,677, U.S. Patent & Trademark Office, pp. 1-11, Feb. 7, 2011.

Chinese Office Action issued in Application No. 200580044086.7, pp. 1-6, Dec. 31, 2010.

* cited by examiner

KINASE INHIBITORS

This application is a 371 of PCT/US2005/041945 filed Nov. 17, 2005 which claims benefit of U.S. Provisional Application 60/629,176 filed Nov. 17, 2004.

FIELD OF THE INVENTION

The present invention is in the field of medicinal chemistry and relates to protein kinase inhibitors, compositions comprising such inhibitors, and methods of use, thereof. More particularly, the invention relates to inhibitors of Aurora-A (Aurora-2) protein kinase. The invention also relates to methods of treating diseases associated with protein kinases, especially diseases associated with Aurora-A, such as cancer.

References

The following publications are cited in this application:

Graham et al. (2002) *J. Biol. Chem.* 277:42419-22.
Warner et al. (2003) *Molecular Cancer Therapeutics* 2:589-95.
Sakai et al. (2002) *J. Biol. Chem.* 277:48714-23.
Sen et al. (2002) *J. Nat. Cancer. Inst.* 94:1320-29.
Castro et al. (2003) *J. Biol. Chem.* 2236-41.
Scrittori et al. (2001) *J. Biol. Chem.* 276:30002-10.
Zhang et al. (2004) *Blood* 103:3717-26).
Brown et al. (2004) *BMC Evolutionary Biology* 4:39.
Warner et al. (2003) *Molecular Cancer Therapeutics* 2:589-95.
Harrington et al. (2004) *Nat. Med.* 10:262-67.
U.S. Pat. No. 6,653,301 (Bebbington) issued Nov. 25, 2003.
Hauf et al. (2003) *J. Cell. Biol.* 161:281-294.
Ditchfield et al. (2003) *J. Cell. Biol.* 161:267-280.
T. W. Greene and G. M. Wuts, *Protecting Groups in Organic Synthesis*, Third Edition, Wiley, New York, 1999.
Fieser and Fieser's Reagents for Organic Synthesis, Volumes 1-15 (John Wiley and Sons, 1991).
Rodd's Chemistry of Carbon Compounds, Volumes 1-5 and Supplementals (Elsevier Science Publishers, 1989).
Organic Reactions, Volumes 1-40 (John Wiley and Sons, 1991).
March's Advanced Organic Chemistry, (John Wiley and Sons, 4$^{th}$ Edition).
Larock's Comprehensive Organic Transformations (VCH Publishers Inc., 1989).
U.S. Pat. No. 5,023,252.
U.S. Pat. No. 5,011,472

All of the above publications are incorporated herein by reference in their entirety to the same extent as if each individual publication, patent or patent application was specifically and individually indicated to be incorporated by reference in its entirety.

State Of The Art

The Aurora kinases are a family of serine/threonine protein kinases associated with mitosis. Members of the family demonstrate distinct subcellular localization during mitosis and are degraded by the proteosome following exit from mitosis (Graham et al. (2002) *J. Biol. Chem.* 277:42419-22). The kinases are often found complexed with other proteins, including cytoskeletal structures. The Aurora kinases share a conserved C-terminal catalytic domain, with greater variation being observed at the N-terminus. Aurora-A (Aurora-2) is unique in the presence of two lysine residues in the nucleotide-binding domain of the kinase (Warner et al. (2003) *Molecular Cancer Therapeutics* 2:589-95).

Maximum levels of the Aurora-A polypeptide, and maximum Aurora-A activity, are observed at the $G_2/M$ transition leading into mitotic prophase, with the polypeptide localizing to the mitotic spindle pole (Graham et al. (2002) *J. Biol. Chem.* 277:42419-22; Sakai et al. (2002) *J. Biol. Chem.* 277:48714-23). Aurora A appears to regulate chromosome duplication with aberrant expression being associated with aneuploidy and an aggressive clinical phenotype, particularly in solid tumors. Such observations, and additional experimental data, suggest that in abnormal cells Aurora-A disrupts the signaling cascade that regulates chromosome segregation (Sen et al. (2002) *J. Nat. Cancer. Inst.* 94:1320-29).

Aurora-A also appears to function in meiosis, likely in separating homologous chromosomes and in spindle rotation. Injection of antibodies against Aurora-A into *Xenopus* oocytes prevents first polar body extrusion and causes arrest at meiosis I (Castro et al. (2003) *J. Biol. Chem.* 2236-41). The *Xenopus* kinesin-like protein, Eg5, is known to be a substrate for Aurora-A (Id.).

In addition, in vitro studies show that Aurora-A is incorporated into chromatin and phosphorylates histone H3, and possibly histone H2B (Scrittori et al. (2001) *J. Biol. Chem.* 276:30002-10). H3 phosphorylation, e.g., at serine-10, during chromosome assembly, appears to be a conserved event in eukaryotic cell division. Inhibition of H3 phosphorylation leads to chromosome condensation, abnormal segregation, and the loss of chromosomes during mitosis and meiosis (Id.).

Accordingly, the emerging model for histone phosphorylation is analogous to that of histone acetylation, wherein partially redundant enzymatic activities are associated with histone modifications but different enzymes may function in different cellular contexts. For example, some enzymes may modify histones in bulk, while other enzymes modify histones in a targeted manner, i.e., in a sequence or domain-specific manner in the context of assembled chromatin (see, e.g., Scrittori et al. (2001) *J. Biol. Chem.* 276:30002-10). In this model, Aurora-A appears to be a kinase responsible for targeted histone modification, in the context of assembled or assembling chromatin.

Other members of the Aurora kinase family are associated with mitosis and meiosis. For example, Aurora-B (Aurora-1) appears to play a role in maintaining the metaphase plate during mitosis, chromatid separation during anaphase and telophase, and even in cytokinesis. Moreover, Aurora-B appears to regulate metaphase I exit and metaphase I plate rotation, during meiosis, suggesting multiple discrete but related roles for the kinase. Aurora-B also appears to associate with a survivin, a polypeptide that associates with the inner centromere and undergoes a significant degree of stretching during mitosis. Survivin appears to be involved with inhibition of apoptosis as well as cell cycle control. Interestingly, both Aurora-B and survivin are delocalized during megakaryocyte endomitosis, a process by which late anaphase and cytokinesis are skipped, leading to megakaryocyte polyploidy (Zhang et al. (2004) *Blood* 103:3717-26).

Aurora-C (Aurora-3) is the least studied, known member, of the family. Aurora-3 localizes to centrosomes from anaphase until telophase (or even cytokinesis), and is highly expressed in the testis (Brown et al. (2004) *BMC Evolutionary Biology* 4:39).

As noted above, Aurora kinases are overexpressed in certain types of cancers, including colon, breast, and other solid-tumor cancers. The genes encoding the Aurora-A and -B kinases tend to be amplified in certain types of cancers, while the gene encoding the Aurora-C kinase resides in a region of the chromosome that is subject to rearrangement and deletion. Aurora-2 has been associated with a variety of malignancies, including primary colon, colorectal, breast, gastric, ovarian, prostate, and cervical cancer, neuroblastoma, and other solid-tumor cancers (Warner et al. (2003) *Molecular Cancer Therapeutics* 2:589-95).

Inhibitors of Aurora-2 have been described. For example, Harrington et al. ((2004) *Nat. Med.* 10:262-67) have described VX-680, a small-molecule inhibitor that blocks cell-cycle progression and induces apoptosis in certain types of tumors in in vivo xenograft models. A pyrazole Aurora-2 kinase inhibitor is also described in U.S. Pat. No. 6,653,301 (Bebbington et al., issued Nov. 25, 2003).

Hauf et al. ((2003) *J. Cell. Biol.* 161:281-294) identified the indolinone, Hesperadin, as an inhibitor Aurora B, which causes cells to enter anaphase with monooriented chromosomes, having both sister kinetochores attached to a single spindle pole (a condition known as syntelic attachment).

Ditchfield et al. ((2003) *J. Cell. Biol.* 161:267-280) described ZM447439 ((4-(4-(N-benzoylamino)anilino)-6-methoxy-7-(3-(1-morpholino)propoxy)quinazoline), an Aurora kinase inhibitor which interferes with chromosome alignment, segregation, and cytokinesis.

Accordingly, kinase inhibitors, particularly inhibitors of Aurora-2 kinase are of particular interest in treating certain disorders, including cancer, compounds exhibiting such inhibition are of particular value.

SUMMARY OF THE INVENTION

This invention is directed to compounds and pharmaceutical compositions that are effective as protein kinase inhibitors, particularly as inhibitors of the Aurora kinases, and most particularly as inhibitors of Aurora-A kinase (Aurora-2). This invention is also directed to methods for treating or preventing a disease mediated at least in part by a protein kinase and, in particular, Aurora-2 using the compounds and/or pharmaceutical compositions of this invention.

This application claims the benefit of U.S. 60/629,176 filed Nov. 17, 2004 which is herein incorporated by reference in its entirety for all purposes.

Accordingly, in one of its compound aspects, this invention is directed to a compound of formula Ia or Ib:

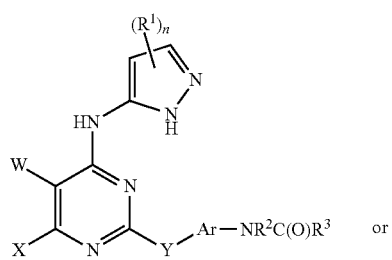

Ia

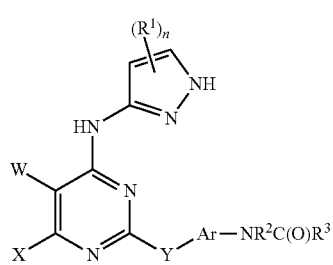

Ib wherein Ar is selected from the group consisting of aryl, substituted aryl, heteroaryl, and substituted heteroaryl;

W is selected from the group consisting of amino and substituted amino;

X is selected from the group consisting of carboxyl, carboxyl esters, and aminoacyl;

Y is selected from the group consisting of oxygen, sulfur, —S(O)—, —S(O)$_2$—, and —NR$^y$— where R$^y$ is selected from the group consisting of hydrogen, alkyl and substituted alkyl;

each R$^1$ is independently selected from the group consisting of acylamino, alkyl, substituted alkyl, alkoxy, substituted alkoxy, aminoacyl, aryl, substituted aryl, aryloxy, substituted aryloxy, carboxyl, carboxyl esters, cycloalkyl, substituted cycloalkyl, halo, cyano, nitro, hydroxyl, heteroaryl, substituted heteroaryl, heteroaryloxy, substituted heteroaryloxy, heterocyclic, and substituted heterocyclic;

R$^2$ is selected from the group consisting of hydrogen and alkyl;

R$^3$ is selected from the group consisting of hydrogen, alkyl; substituted alkyl, alkoxy, substituted alkoxy, amino, substituted amino, cycloalkyl, substituted cycloalkyl, cycloalkoxy, substituted cycloalkoxy, aryl, substituted aryl, aryloxy, substituted aryloxy, cycloalkoxy, substituted cycloalkoxy, heteroaryl, substituted heteroaryl, heteroaryloxy, substituted heteroaryloxy, heterocyclic, substituted heterocyclic, heterocycloxy, and substituted heterocycloxy; and n is an integer equal to 0, 1 or 2;

or isomers, prodrugs, or pharmaceutically acceptable salts thereof.

DETAILED DESCRIPTION OF THE INVENTION

Definitions

Unless otherwise limited by a specific recitation herein, the following terms have the following meanings;

"Alkyl" refers to monovalent alkyl groups having from 1 to 10 carbon atoms, preferably from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to a monovalent alkyl group having from 1 to 3, and preferably 1 to 2, substituents selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, thiol, alkylthiol, substituted alkyl thiol, trialkylsilyl, nitro, carboxyl, carboxyl esters, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Aminoacyl" refers to the group —C(O)NR$^{10}$R$^{10}$ where each R$^{10}$ is independently selected from the group consisting of hydrogen, alkyl, substituted alkyl, alkenyl, substituted alkenyl, aryl, substituted aryl, cycloalkyl, substituted cycloalkyl, heteroaryl, substituted heteroaryl, heterocyclic, substituted heterocyclic and where each R$^{10}$ is joined to form together with the nitrogen atom a heterocyclic or substituted heterocyclic ring.

"Alkenyl" refers to a monovalent alkenyl group having from 2 to 6 carbon atoms and more preferably 2 to 4 carbon atoms and having at least 1 and preferably from 1-2 sites of alkenyl unsaturation. The term "alkenyl" encompasses any and all combinations of cis and trans isomers arising from the presence of unsaturation.

"Substituted alkenyl" refers to alkenyl groups having from 1 to 3 substituents, and preferably 1 to 2 substituents, selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic provided that any hydroxyl substitution is not on a vinyl carbon atom.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocylic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino.

"Acylamino" refers to the groups —$NR^{11}$C(O)alkyl, —$NR^{11}$C(O)substituted alkyl, —$NR^{11}$C(O)cycloalkyl, —$NR^{11}$C(O)substituted cycloalkyl, —$NR^{11}$C(O)alkenyl, —$NR^{11}$C(O)substituted alkenyl, —$NR^{11}$C(O)aryl, —$NR^{11}$C(O)substituted aryl, —$NR^{11}$C(O)heteroaryl, —$NR^{11}$C(O)substituted heteroaryl, —$NR^{11}$C(O)heterocyclic, and —$NR^{11}$C(O)substituted heterocyclic where $R^{11}$ is hydrogen or alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is to an aromatic ring atom. Preferred aryls include phenyl and naphthyl, e.g, 2-naphthyl.

"Substituted aryl" refers to aryl groups which are substituted with from 1 to 3 substituents, and preferably 1 to 2 substituents, selected from the group consisting of hydroxy, acyl, acylamino, alkyl, substituted alkyl, alkoxy, substituted alkoxy, alkenyl, substituted alkenyl, amino, substituted amino, aminoacyl, aryl, substituted aryl, aryloxy, substituted aryloxy, cycloalkoxy, substituted cycloalkoxy, carboxyl, carboxyl esters, cyano, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Carboxyl" or "carboxy" refers to —COOH or pharmaceutically acceptable salts thereof.

"Carboxyl esters" refers to the groups —C(O)O-alkyl, —C(O)O-substituted alkyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclyl, and —C(O)O-substituted heterocyclyl wherein alkyl, substituted alkyl, aryl substituted aryl, cycloalkyl, substituted cycloalkyl, heterocyclyl, and substituted heterocyclyl are as defined herein.

"Cycloalkyl" refers to monovalent cyclic alkyl groups of from 3 to 10 carbon atoms having single or multiple condensed rings which condensed rings may or may not be cycloalkyl provided that the point of attachment is to a cycloalkyl ring atom. Examples of cycloalkyl groups include, by way of example, adamantyl, cyclopropyl, cyclobutyl, cyclopentyl, cyclooctyl and the like.

"Substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Heteroaryl" refers to a monovalent aromatic group of from 1 to 15 carbon atoms, preferably from 1 to 10 carbon atoms, and 1 to 4 heteroatoms selected from the group consisting of oxygen, nitrogen, and sulfur within the ring. The nitrogen and sulfur ring atoms can be optionally oxidized. Such heteroaryl groups can have a single ring (e.g., pyridyl or furyl) or multiple condensed rings (e.g., indolizinyl or benzothienyl) provided that the point of attachment is through an aromatic ring atom. Preferred heteroaryls include pyridyl, pyrrolyl, indolyl, thiophenyl, and furyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" refers to a monovalent saturated or unsaturated non-aromatic group having a single ring or multiple condensed rings, from 1 to 10 carbon atoms and from 1 to 4 hetero atoms selected from the group consisting of nitrogen, sulfur, or oxygen within the ring wherein, in fused ring systems, one or more the rings can be aryl or heteroaryl provided that the point of attachment is to a heterocyclic (non-aromatic) ring atom. In addition, the nitrogen and sulfur ring atoms can be optionally oxidized.

"Substituted heterocyclic" refers to heterocyclic groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Thiol" and "thio" refers to —SH group.

"Alkylthiol" refers to thiol groups substituted with alkyl groups.

"Substituted alkylthiol" refers to thiol groups substituted with substituted alkyl groups.

"Trialkylsilyl" refers to an Si group substituted with three alkyl groups, wherein each of the alkyl groups may the same or different.

"Isomer" and "isomers" refer to geometric, stereoisomeric, and tautomeric isomers of a compound. Geometric isomers refer to compounds that differ in the cis or trans orientation of one or more double bonds. Stereoisomers refer to compounds that differ in the chirality of one or more stereocenters and include enantiomers and diastereomers. Tautomers refer to alternate forms of a molecule that differ in the position of a proton, such as enol-keto and imine-enamine tautomers, or the tautomeric forms of heteroaryl groups containing a ring atom attached to both a ring —NH— moiety and a ring =N— moeity such as pyrazoles, imidazoles, benzimidazoles, triazoles, and tetrazoles.

"Pharmaceutically acceptable salt" refers to pharmaceutically acceptable salts of a compound of Formula Ia, Ib, IIa, IIb, IIIa or IIIb which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Patient" refers to human and non-human mammals.

"Prodrug" refers to compounds that are rapidly transformed in vivo to yield the parent compound of the above formula, for example by hydrolysis in blood. A discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. "Pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention.

Various other terms are used in the disclosure to refer to different aspects of mitotis, meiosis, cytokinesis, cell proliferation, cancer and malignancy. Unless otherwise indicated, all scientific terms are to be given their usual meaning, as known in the relevant art.

Compounds of the invention are useful for inhibiting the activity of serine/threonine protein kinases, particularly the Aurora kinases, and most particularly Aurora-1 (Aurora-B) or Aurora-2 kinase (Aurora-A).

Aurora-1 and Aurora 2 regulate chromosome duplication. Aberrant expression of Aurora-2 is associated with aneuploidy and malignancy. Accordingly, the compounds of the instant invention are useful for modulating chromosome duplication and aberrant cell proliferation. In a particular embodiment of the invention, the compounds of the invention are used to reduce the rate of cell proliferation or to prevent cell proliferation, e.g., by interfereing with chromosome duplication. In a particular embodiment of the invention, the compounds of the invention cause cell death, preferably via apoptosis but optionally via necrosis.

The instant inhibitors are also useful for inhibiting the phosphorylation of histones, particularly histone H3, and particularly during chromatin assembly. Inhibition of H3 phosphorylation leads to chromosome condensation, abnormal segregation, and the loss of chromosomes during mitosis and meiosis. Thus, the instant compounds are useful for modulating cell propliferation by interfering with mitosis and meiosis. In one embodiment of the invention, the treatment of cells with the compounds of the invention results in reduced cell proliferation. In another embodiment, the treatment of cells with the compounds of the invention results in cell death. In particular embodiment of the invention, the treatment of cells with the compounds of the invention results in apoptosis. Alternatively, treatment of the cells results in necrosis.

Inhibitors of Aurora-1 or Aurora-2 are used to inhibit mitosis and/or meiosis. Thus the instant inhibitors may be used to modulate the proliferation of somatic cells or modulate meiosis in gametes or related cells. In a particular embodiment of the invention, the inhibitors are used to arrest metaphase I exit in meiotic cells. As indicated above, treatment of the cells may arrest or attenuate cell proliferation, and may result in cell death by apoptosis or necrosis.

The instant Aurora kinase inhibitors are used in modulating megakaryocyte polyploidy. In a preferred embodiment of the invention, the inhibitors are used to promote megakaryocyte polyploidy by interfering with the normal biological role of Aurora-2 in such cells.

Because aberrant expression of the Aurora kinases has been associated with various cancers, the inhibitors of the invention are useful for treating cancers by modulating cancer cell proliferation. In one embodiment of the invention, the inhibitors are administered to a patient to treat a cancer such as primary colon, colorectal, breast, gastric, ovarian, prostate, and cervical cancer, neuroblastoma, and/or other solid-tumor cancers. This list is by no means exhaustive. Since the Aurora kinases appear to be general regulators of mitosis and meiosis, inhibition of the Aurora kinases is likely to modulate the proliferation of many cell types. Therefore, the compounds of this invention will be effective in treating a broad range of cancers, including but not limited to those identified, herein.

The inhibitors of the invention can be administered in combination with any known cancer therapies, provided that the two or more therapies are not contraindicated as a result of toxicity or other pharmacological issues, particularly those which involve liver function. Examples of such cancer therapies include surgery, chemotherapy, and radiation therapy, as well as emerging therapies involving antibodies, naturally occurring and synthetic small-molecules, metabolic analogs, gene therapy, etc. For example, it may desirable to combine a kinase inhibitor of the invention with a drug specific for a different biological target, thereby increasing the opportunity to interfere with aberrant cancer cell proliferation.

Accordingly, in one of its compound aspects, this invention is directed to a compound of formula Ia or Ib:

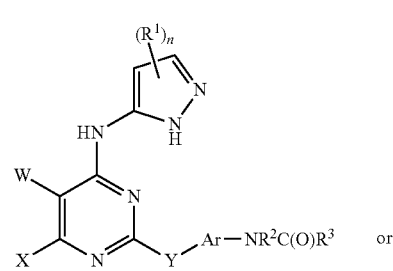

Ia

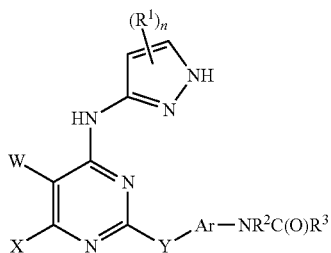

Ib wherein Ar is selected from the group consisting of aryl, substituted aryl, heteroaryl, and substituted heteroaryl;

W is selected from the group consisting of amino and substituted amino;

X is selected from the group consisting of carboxyl, carboxyl esters, and aminoacyl;

Y is selected from the group consisting of oxygen, sulfur, —S(O)—, —S(O)$_2$—, and —NR$^y$— where R$^y$ is selected from the group consisting of hydrogen, alkyl and substituted alkyl;

each R$^1$ is independently selected from the group consisting of acylamino, alkyl, substituted alkyl, alkoxy, substituted alkoxy, aminoacyl, aryl, substituted aryl, aryloxy, substituted aryloxy, carboxyl, carboxyl esters, cycloalkyl, substituted cycloalkyl, halo, cyano, nitro, hydroxyl, heteroaryl, substituted heteroaryl, heteroaryloxy, substituted heteroaryloxy, heterocyclic, and substituted heterocyclic;

R$^2$ is selected from the group consisting of hydrogen and alkyl;

R$^3$ is selected from the group consisting of hydrogen, alkyl; substituted alkyl, alkoxy, substituted alkoxy, amino, substituted amino, cycloalkyl, substituted cycloalkyl, cycloalkoxy, substituted cycloalkoxy, aryl, substituted aryl, aryloxy, substituted aryloxy, cycloalkoxy, substituted cycloalkoxy, heteroaryl, substituted heteroaryl, heteroaryloxy, substituted heteroaryloxy, heterocyclic, substituted heterocyclic, heterocycloxy, and substituted heterocycloxy; and n is an integer equal to 0, 1 or 2;

or isomers, prodrugs, or pharmaceutically acceptable salts thereof.

In a preferred embodiment, Y is —S—, —S(O)— or —S(O)$_2$—.

In a preferred embodiment, W is amino.

In another of its compound aspects, this invention is directed to a compound of formula IIa or IIb:

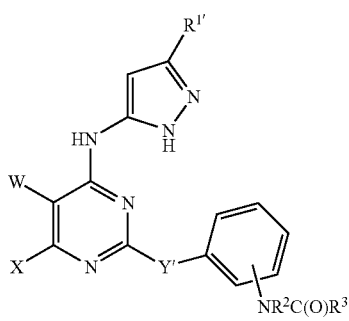

IIa

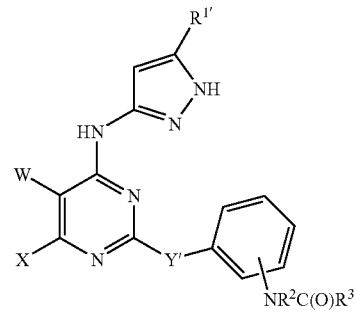

IIb wherein:

W is selected from the group consisting of amino and substituted amino;

X is selected from the group consisting of carboxyl, carboxyl esters, and aminoacyl;

Y' is selected from the group consisting of sulfur, —S(O)—, and —S(O)$_2$—;

R$^{1'}$ is selected from the group consisting of hydrogen, acylamino, alkyl, substituted alkyl, alkoxy, substituted alkoxy, aminoacyl, aryl, substituted aryl, aryloxy, substituted aryloxy, carboxyl, carboxyl esters, cycloalkyl, substituted cycloalkyl, halo, cyano, nitro, hydroxyl, heteroaryl, substituted heteroaryl, heteroaryloxy, substituted heteroaryloxy, heterocyclic, and substituted heterocyclic;

R$^2$ is selected from the group consisting of hydrogen and alkyl; and

R$^3$ is selected from the group consisting of hydrogen, alkyl, substituted alkyl, alkoxy, substituted alkoxy, amino, substituted amino, cycloalkyl, substituted cycloalkyl, cycloalkoxy, substituted cycloalkoxy, aryl, substituted aryl, aryloxy, substituted aryloxy, heteroaryl, substituted heteroaryl, heteroaryloxy, substituted heteroaryloxy, heterocyclic, substituted heterocyclic, heterocycloxy, and substituted heterocycloxy;

or isomers, prodrugs, or pharmaceutically acceptable salts thereof.

In still another of its compound aspects, this invention is directed to a compound of formula IIIa or IIIb:

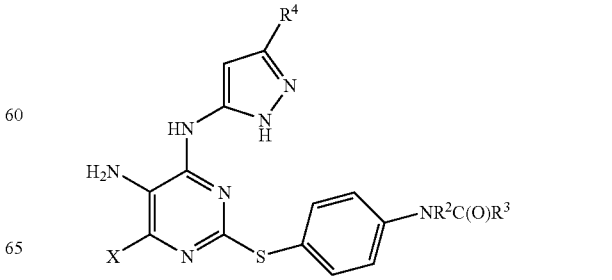

IIIa

-continued

IIIb

[Structure: Pyrimidine core with R⁴-substituted pyrazole via NH, H₂N, X, and S-phenyl-NR²C(O)R³ substituents]

wherein:

X is selected from the group consisting of carboxyl, carboxyl esters, and aminoacyl;

R² is selected from the group consisting of hydrogen and alkyl;

R³ is selected from the group consisting of hydrogen, alkyl, substituted alkyl, alkoxy, substituted alkoxy, amino, substituted amino, cycloalkyl, substituted cycloalkyl, cycloalkoxy, substituted cycloalkoxy, aryl, substituted aryl, aryloxy, substituted aryloxy, heteroaryl, substituted heteroaryl, heteroaryloxy, substituted heteroaryloxy, heterocyclic, substituted heterocyclic, heterocycloxy, and substituted heterocycloxy; and R⁴ is selected from the group consisting of alkyl and substituted alkyl;

or isomers, prodrugs, or pharmaceutically acceptable salts thereof.

In a preferred embodiment, R¹ is alkyl or substituted alkyl. More preferably, R¹ and R⁴ are alkyl and most preferably are methyl.

In a preferred embodiment, R² is hydrogen.

In a preferred embodiment, R³ is alkyl, substituted alkyl, cycloalkyl or substituted cycloalkyl. More preferably, R³ is cycloalkyl and most preferably R³ is cyclopropyl.

Preferred X groups include:

—CO₂H, —CO₂CH₃, —CO₂CH₂CH₃,

[Various X group structures shown including amides and esters with CH₃, CH₂CH₂N(CH₃)₂, piperidinylethyl, morpholinylethyl ester, tetrahydropyranyl ester, CH₂CH₂OCH₃ ester, CH₂CH₂SCH₃ ester, cyclohexyl ester, CH₂CH₂OCH₃ amide, morpholine amide, thiomorpholine amide, CH₂CH₂N(CH₃)₂ ester, isopropyl ester, CH₂CH₂OH ester, pyridin-4-yl amide, morpholinylethyl amide, piperidine amide, tetrahydrofurfuryl amide, CH₂CH₂CH₂OCH₃ amide, CH₂CH₂SCH₃ amide, tert-butyl amide, furfuryl amide, thienylmethyl amide, 1-methoxypropan-2-yl amide, phenyl amide, cyclohexyl amide, tetrahydropyran-3-yl amide, 1-methylpiperidin-4-yl amide, CH₂CF₃ amide, benzyl ester, CH₂CH₂Si(CH₃)₃ ester, 4-methylpiperazine amide]

and the like.

Compounds of this invention include those set forth in Table I below as well as tautomers and pharmaceutically acceptable salts thereof:

TABLE I

| Cmpd. No. | Structure | Name |
| --- | --- | --- |
| 7 | 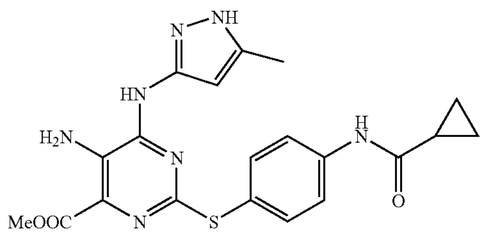 | methyl 2-(4-cyclopropane-carboxamidophenylsulfanyl)-5-amino-6-(5-methylpyrazol-3-ylamino)-4-pyrimidinecarboxylate |
| 8 | 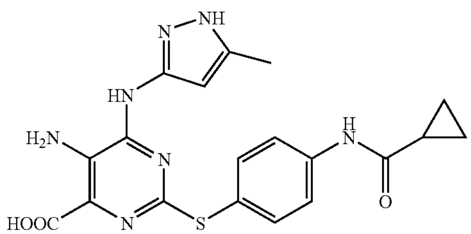 | 2-(4-cyclopropanecarbox-amidophenylsulfanyl)-5-amino-6-(5-methylpyrazol-3-ylamino)-4-pyrimidinecarboxylic acid |
| 9 | 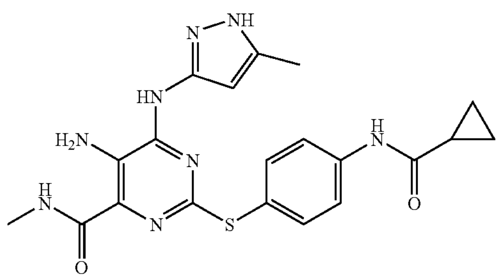 | N-methyl-2-(4-cyclopropane-carboxamidophenylsulfanyl)-5-amino-6-(5-methylpyrazol-3-ylamino)-4-pyrimidine carboxamide |
| 11 | 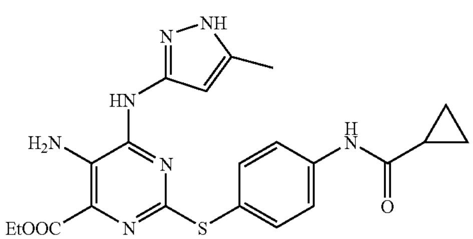 | ethyl 2-(4-cyclopropane-carboxamidophenylsulfanyl)-5-amino-6-(5-methylpyrazol-3-ylamino)-4-pyrimidine carboxylate |
| 12 | 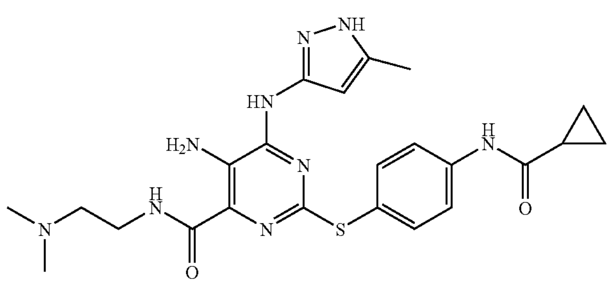 | N-[2-(N,N-dimethylamino)-ethyl]-2-(4-cyclopropane-carboxamidophenylsulfanyl)-5-amino-6-(5-methylpyrazol-3-ylamino)-4-pyrimidine carboxamide |
| 13 | 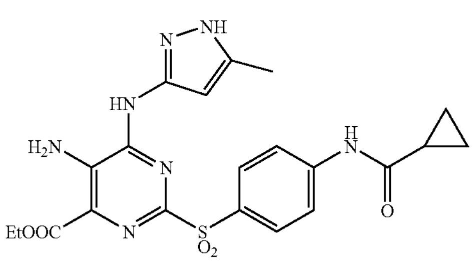 | ethyl 2-(4-cyclopropane-carboxamidophenylsulfonyl)-5-amino-6-(5-methylpyrazol-3-ylamino)-4-pyrimidinecarboxylate |

TABLE I-continued

| Cmpd. No. | Structure | Name |
|---|---|---|
| 14 | 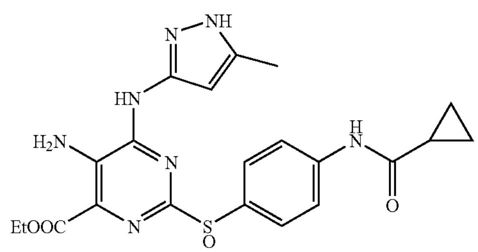 | ethyl 2-(4-cyclopropane-carboxamidophenylsulfinyl)-5-amino-6-(5-methylpyrazol-3-ylamino)-4-pyrimidinecarboxylate |
| 17 | 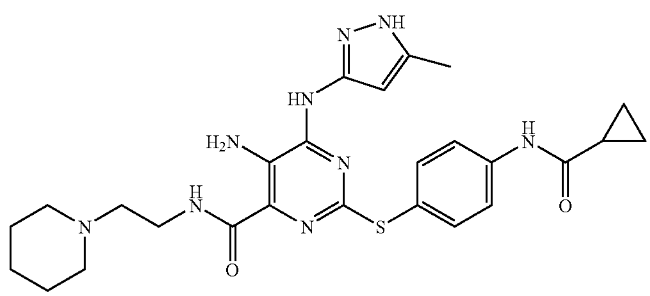 | N-(2-piperidin-1-ylethyl)-2-(4-cyclopropanecarboxamido-phenylsulfanyl)-5-amino-6-(5-methylpyrazol-3-ylamino)-4-pyrimidinecarboxamide |
| 18 | 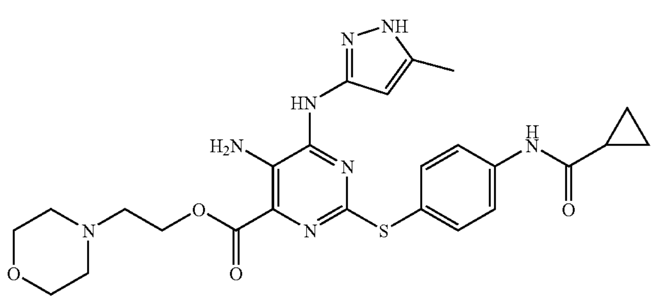 | 2-morpholin-4-ylethyl 2-(4-cyclopropanecarboxamido-phenylsulfanyl)-5-amino-6-(5-methylpyrazol-3-ylamino)-4-pyrimidinecarboxylate |
| 19 | 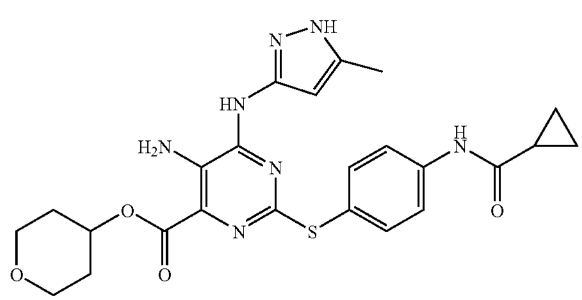 | tetrahydro-2H-pyran-4-yl 2-(4-cyclopropanecarboxamido-phenylsulfanyl)-5-amino-6-(5-methylpyrazol-3-ylamino)-4-pyrimidinecarboxylate |
| 34 | 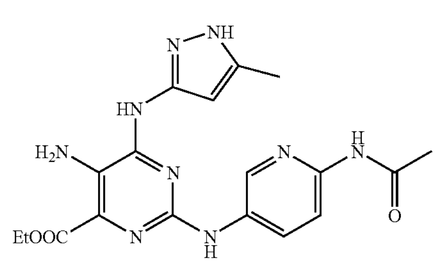 | ethyl 2-(6-acetylamido-3-pyridylamino)-5-amino-6-(5-methylpyrazol-3-ylamino)-4-pyrimidinecarboxylate |

TABLE I-continued

| Cmpd. No. | Structure | Name |
|---|---|---|
| 36 | 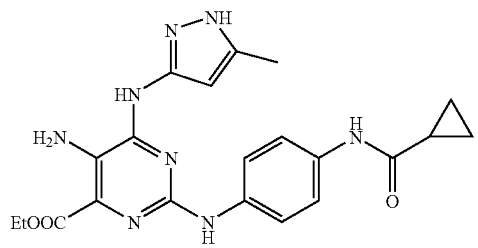 | ethyl 2-({4-[(cyclopropylcarbonyl)amino]phenyl}amino)-5-amino-6-(5-methylpyrazol-3-ylamino)-4-pyrimidinecarboxylate |
| 40 | 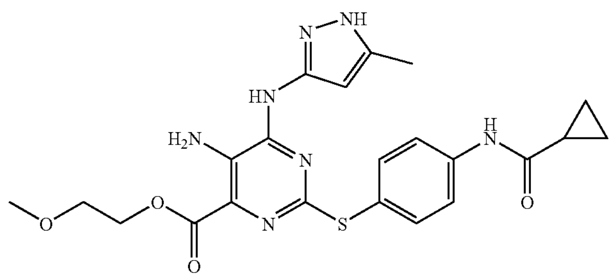 | 2-methoxyethyl 2-(4-cyclopropanecarboxamidophenylsulfanyl)-5-amino-6-(5-methylpyrazol-3-ylamino)-4-pyrimidinecarboxylate |
| 41 | 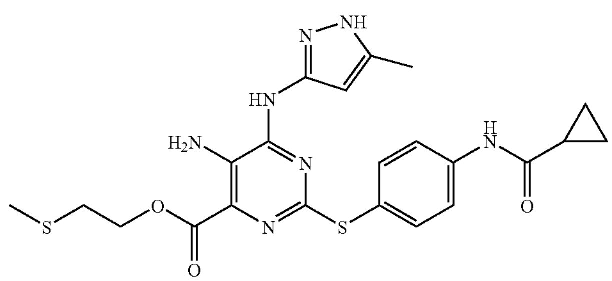 | (2-(methylthio)ethyl 2-(4-cyclopropanecarboxamidophenylsulfanyl)-5-amino-6-(5-methylpyrazol-3-ylamino)-4-pyrimidinecarboxylate |
| 42 | 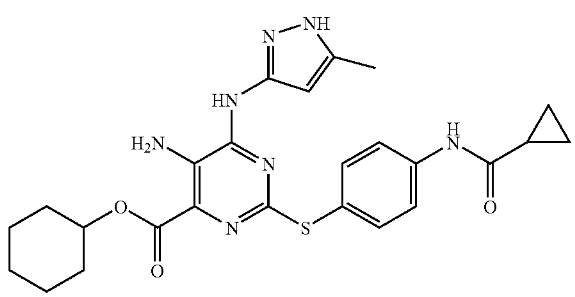 | cyclohexyl 2-(4-cyclopropanecarboxamidophenylsulfanyl)-5-amino-6-(5-methylpyrazol-3-ylamino)-4-pyrimidinecarboxylate |
| 43 | 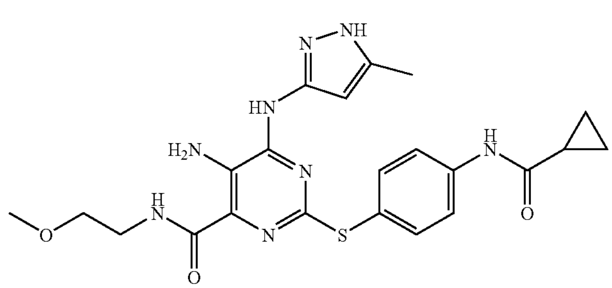 | N-(2-methoxyethyl)-2-(4-cyclopropanecarboxamidophenylsulfanyl)-5-amino-6-(5-methylpyrazol-3-ylamino)-4-pyrimidinecarboxamide |

TABLE I-continued

| Cmpd. No. | Structure | Name |
|---|---|---|
| 44 | 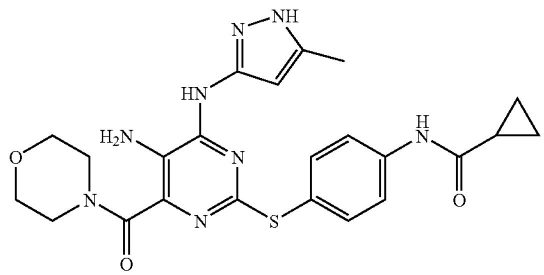 | morpholin-4-yl 2-(4-cyclopropanecarboxamido-phenylsulfanyl)-5-amino-6-(5-methylpyrazol-3-ylamino)-4-pyrimidinecarboxamide |
| 45 | 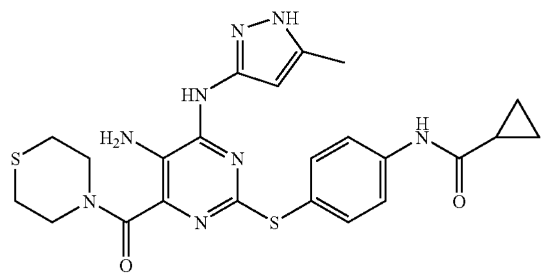 | thiomorpholin-4-yl 2-(4-cyclopropanecarboxamido-phenylsulfanyl)-5-amino-6-(5-methylpyrazol-3-ylamino)-4-pyrimidinecarboxamide |
| 46 | 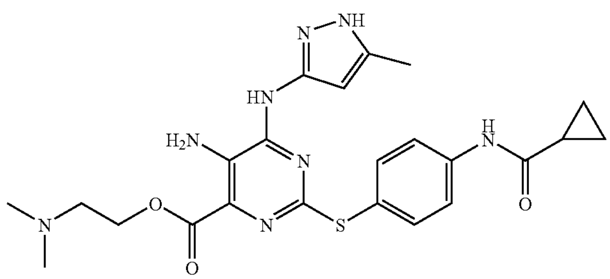 | 2-dimethylaminoethyl 2-(4-cyclopropanecarboxamido-phenylsulfanyl)-5-amino-6-(5-methylpyrazol-3-ylamino)-4-pyrimidinecarboxylate |
| 47 | 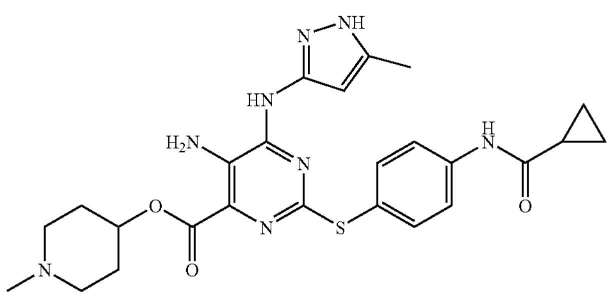 | 1-methylpiperidin-4-yl 2-(4-cyclopropanecarboxamido-phenylsulfanyl)-5-amino-6-(5-methylpyrazol-3-ylamino)-4-pyrimidinecarboxylate |
| 48 | 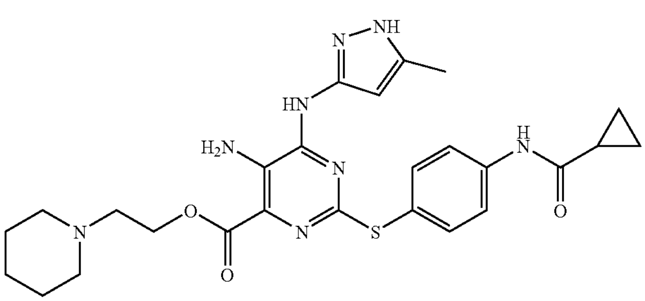 | 2-piperidin-1-ylethyl 2-(4-cyclopropanecarboxamido-phenylsulfanyl)-5-amino-6-(5-methylpyrazol-3-ylamino)-4-pyrimidinecarboxylate |

TABLE I-continued

| Cmpd. No. | Structure | Name |
|---|---|---|
| 49 | 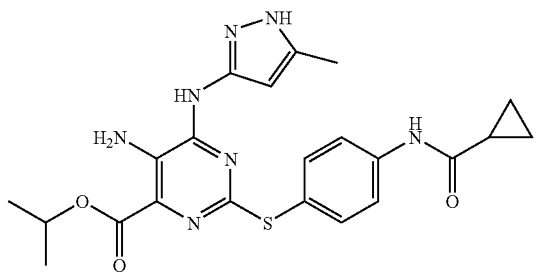 | isopropyl 2-(4-cyclopropane-carboxamidophenylsulfanyl)-5-amino-6-(5-methylpyrazol-3-ylamino)-4-pyrimidinecarboxylate |
| 50 | 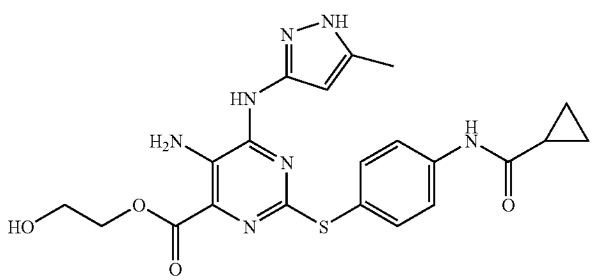 | 2-hydroxyethyl 2-(4-cyclopropanecarboxamido-phenylsulfanyl)-5-amino-6-(5-methylpyrazol-3-ylamino)-4-pyrimidinecarboxylate |
| 51 | 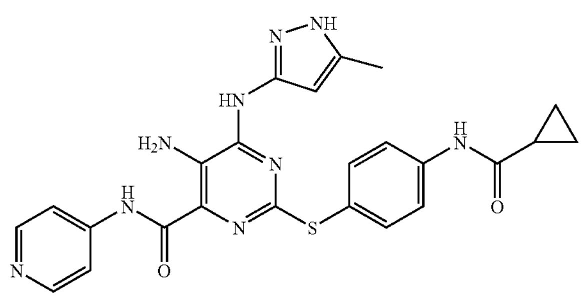 | N-pyridin-4-yl-2-(4-cyclopropanecarboxamido-phenylsulfanyl)-5-amino-6-(5-methylpyrazol-3-ylamino)-4-pyrimidinecarboxamide |
| 52 | 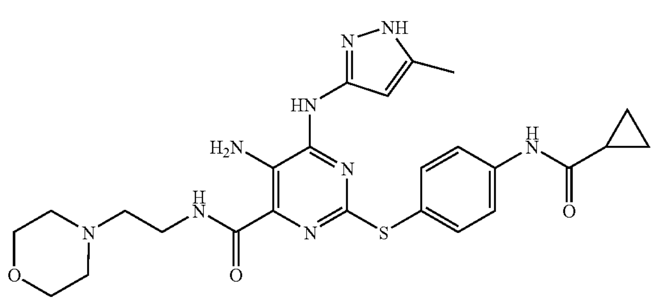 | N-(2-morpholin-4-ylethyl)-2-cyclopropanecarboxamido-phenylsulfanyl)-5-amino-6-(5-methylpyrazol-3-ylamino)-4-pyrimidinecarboxamide |
| 53 | 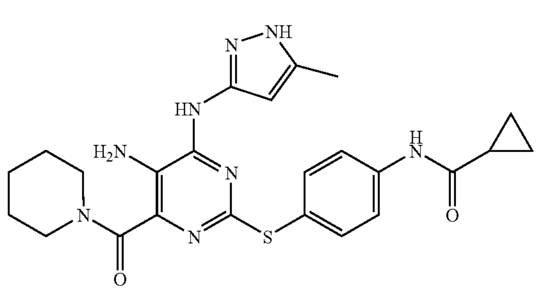 | piperidin-1-yl 2-(4-cyclopropanecarboxamido-phenylsulfanyl)-5-amino-6-(5-methylpyrazol-3-ylamino)-4-pyrimidinecarboxamide |

TABLE I-continued

| Cmpd. No. | Structure | Name |
|---|---|---|
| 54 | 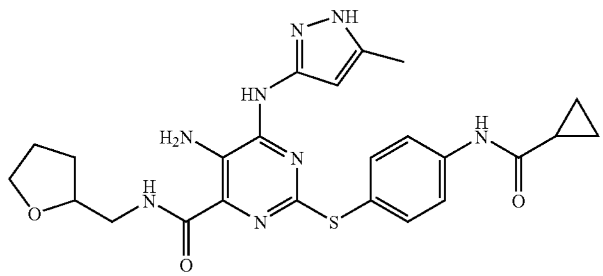 | N-(tetrahydrofuran-2-ylmethyl)-2-(4-cyclopropane-carboxamidophenylsulfanyl)-5-amino-6-(5-methylpyrazol-3-ylamino)-4-pyrimidinecarboxamide |
| 55 | 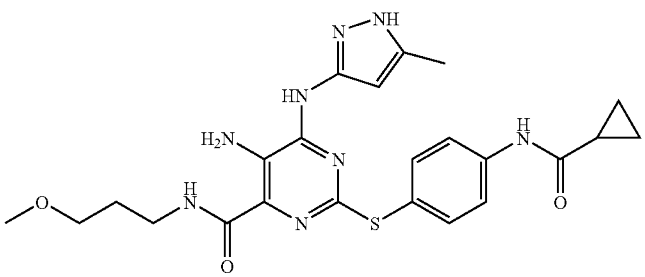 | N-(3-methoxypropyl)-2-(4-cyclopropanecarboxamidophenyl-sulfanyl)-5-amino-6-(5-methylpyrazol-3-ylamino)-4-pyrimidinecarboxamide |
| 56 | 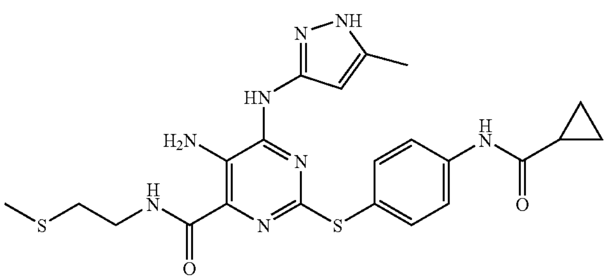 | N-(2-methylthioethyl)-2-(4-cyclopropanecarboxamido-phenylsulfanyl)-5-amino-6-(5-methylpyrazol-3-ylamino)-4-pyrimidinecarboxamide |
| 57 | 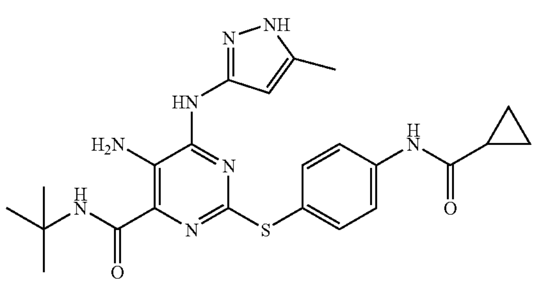 | N-(tert-butyl)-2-(4-cyclopropanecarboxamido-phenylsulfanyl)-5-amino-6-(5-methylpyrazol-3-ylamino)-4-pyrimidinecarboxamide |
| 58 | 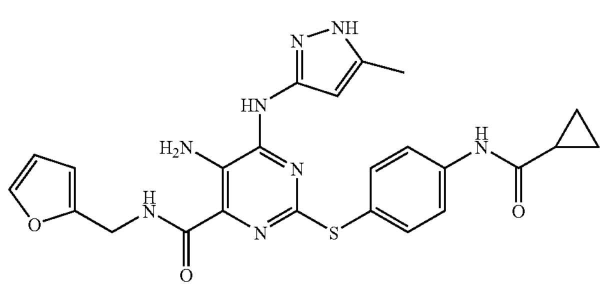 | N-(2-furylmethyl)-2-(4-cyclopropanecarboxamido-phenylsulfanyl)-5-amino-6-(5-methylpyrazol-3-ylamino)-4-pyrimidinecarboxamide |

TABLE I-continued

| Cmpd. No. | Structure | Name |
|---|---|---|
| 59 | 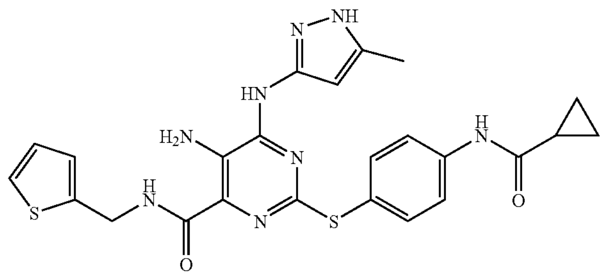 | N-(2-thien-2-ylmethyl)-2-(4-cyclopropanecarboxamido-phenylsulfanyl)-5-amino-6-(5-methylpyrazol-3-ylamino)-4-pyrimidinecarboxamide |
| 60 | 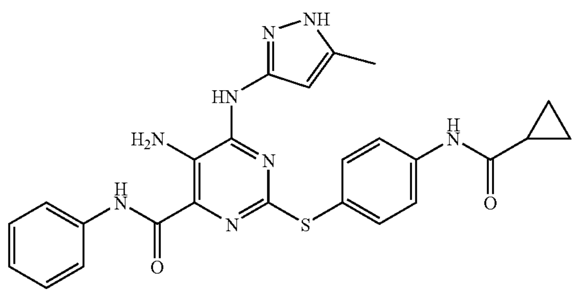 | N-phenyl 2-(4-cyclopropane-carboxamidophenylsulfanyl)-5-amino-6-(5-methylpyrazol-3-ylamino)-4-pyrimidinecarboxamide |
| 61 | 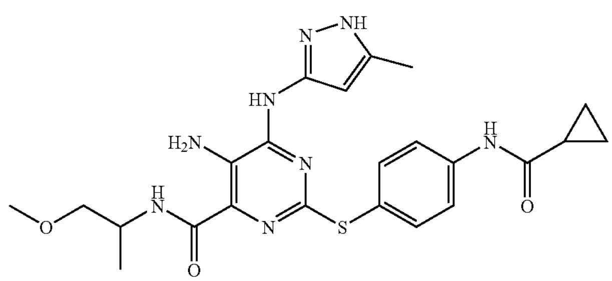 | N-(2-methoxy-1-methylethyl)-2-(4-cyclopropanecarboxamido-phenylsulfanyl)-5-amino-6-(5-methylpyrazol-3-ylamino)-4-pyrimidinecarboxamide |
| 62 | 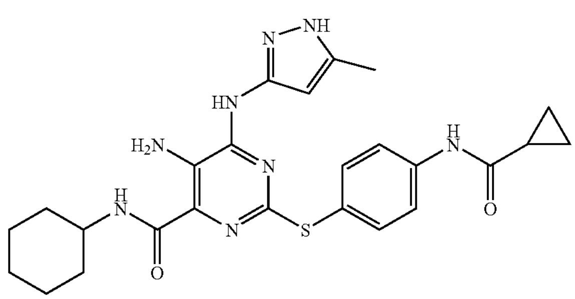 | N-cyclohexyl 2-(4-cyclopropane-carboxamidophenylsulfanyl)-5-amino-6-(5-methylpyrazol-3-ylamino)-4-pyrimidinecarboxamide |
| 63 | 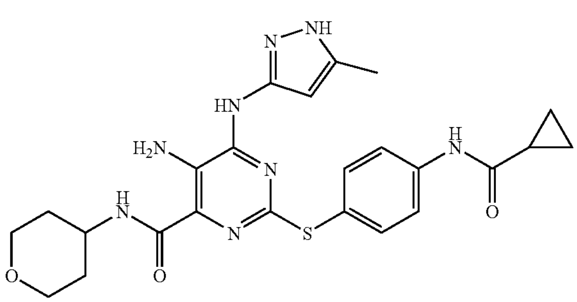 | N-tetrahydro-2H-pyran-4-yl-2-(4-cyclopropanecarboxamido-phenylsulfanyl)-5-amino-6-(5-methylpyrazol-3-ylamino)-4-pyrimidinecarboxamide |

TABLE I-continued

| Cmpd. No. | Structure | Name |
|---|---|---|
| 64 | 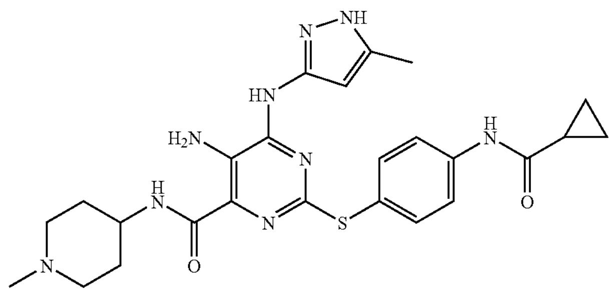 | N-(1-methylpiperidin-4-yl)-2-(4-cyclopropanecarboxamido-phenylsulfanyl)-5-amino-6-(5-methylpyrazol-3-ylamino)-4-pyrimidinecarboxamide |
| 65 | 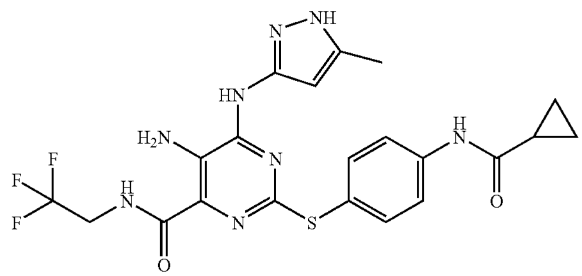 | N-(2,2,2-trifluoroethyl)-2-(4-cyclopropanecarboxamido-phenylsulfanyl)-5-amino-6-(5-methylpyrazol-3-ylamino)-4-pyrimidinecarboxamide |
| 66 | 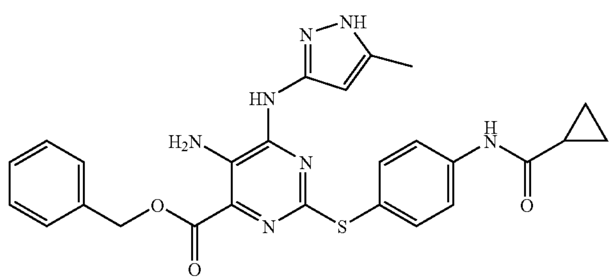 | benzyl 2-(4-cyclopropane-carboxamidophenylsulfanyl)-5-amino-6-(5-methylpyrazol-3-ylamino)-4-pyrimidinecarboxylate |
| 67 | 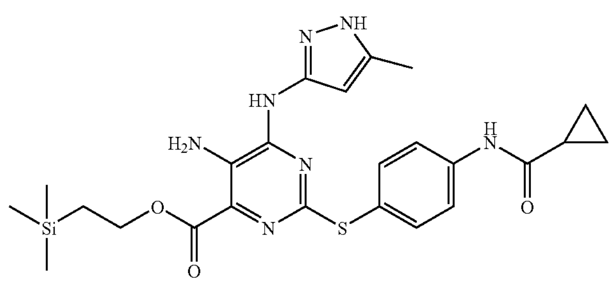 | 2-(trimethylsilyl)ethyl 2-(4-cyclopropanecarboxamido-phenylsulfanyl)-5-amino-6-(5-methylpyrazol-3-ylamino)-4-pyrimidinecarboxylate |
| 68 | 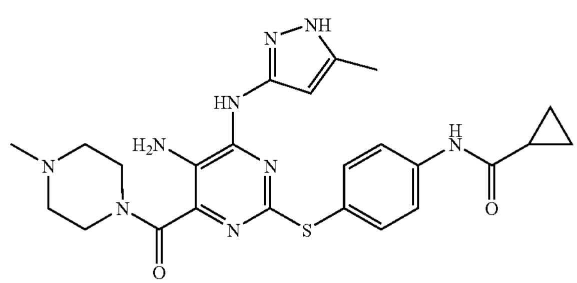 | N-(4-methylpiperazin-1-yl)-2-(4-cyclopropanecarboxamido-phenylsulfanyl)-5-amino-6-(5-methylpyrazol-3-ylamino)-4-pyrimidinecarboxamide |

The compounds of formula Ia, Ib, IIa, IIb, IIIa and IIIb may be formulated into pharmaceutical compositions. Such compositions comprise a pharmaceutically acceptable diluent and an effective amount of one or more of such compounds to prophylactically or therapeutically treat diseases mediated at least in part by a protein kinase, particularly Aurora-A.

The compounds and/or pharmaceutical compositions of this invention are useful in treating or preventing diseases mediated at least in part by a protein kinase, particularly Aurora-A. Such methods comprise administering a compound or mixture of compounds of this invention, preferably in a pharmaceutical composition to a patient in need of such treatment.

Compound Preparation

The compounds of this invention can be prepared from readily available starting materials using, for example, the following general methods and procedures. It will be appreciated that where typical or preferred process conditions (i.e., reaction temperatures, times, mole ratios of reactants, solvents, pressures, etc.) are given, alternative process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

Scheme 1 below illustrates a method for the preparation of the compounds of this invention from starting materials either known in the art or commercially available. For illustrative purposes only, Scheme 1 employs the following substituents: $R^2$ is hydrogen, Y is sulfur, Ar is phenyl, W is amino, and $R^1$, $R^3$ and n are as defined above. In addition, X is illustrated as a carboxyl group, a methyl carboxyl ester group or a methyl carboxamide group. It is understood that variations on $R^2$, Y, Ar, W and X are well within the skill of the art and some of these are discussed below. Further, $R^3$-carbonylamino substitution on the phenyl group for Ar is depicted at the para position. It is understood that such substitution can be placed at either the ortho or meta positions.

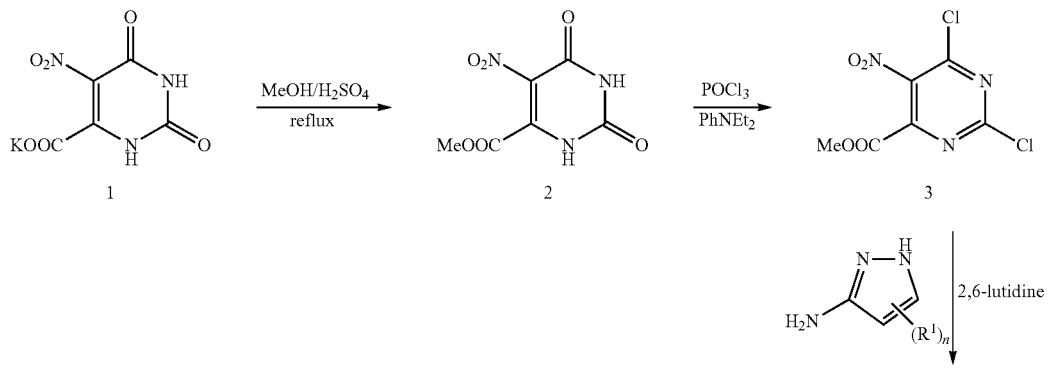

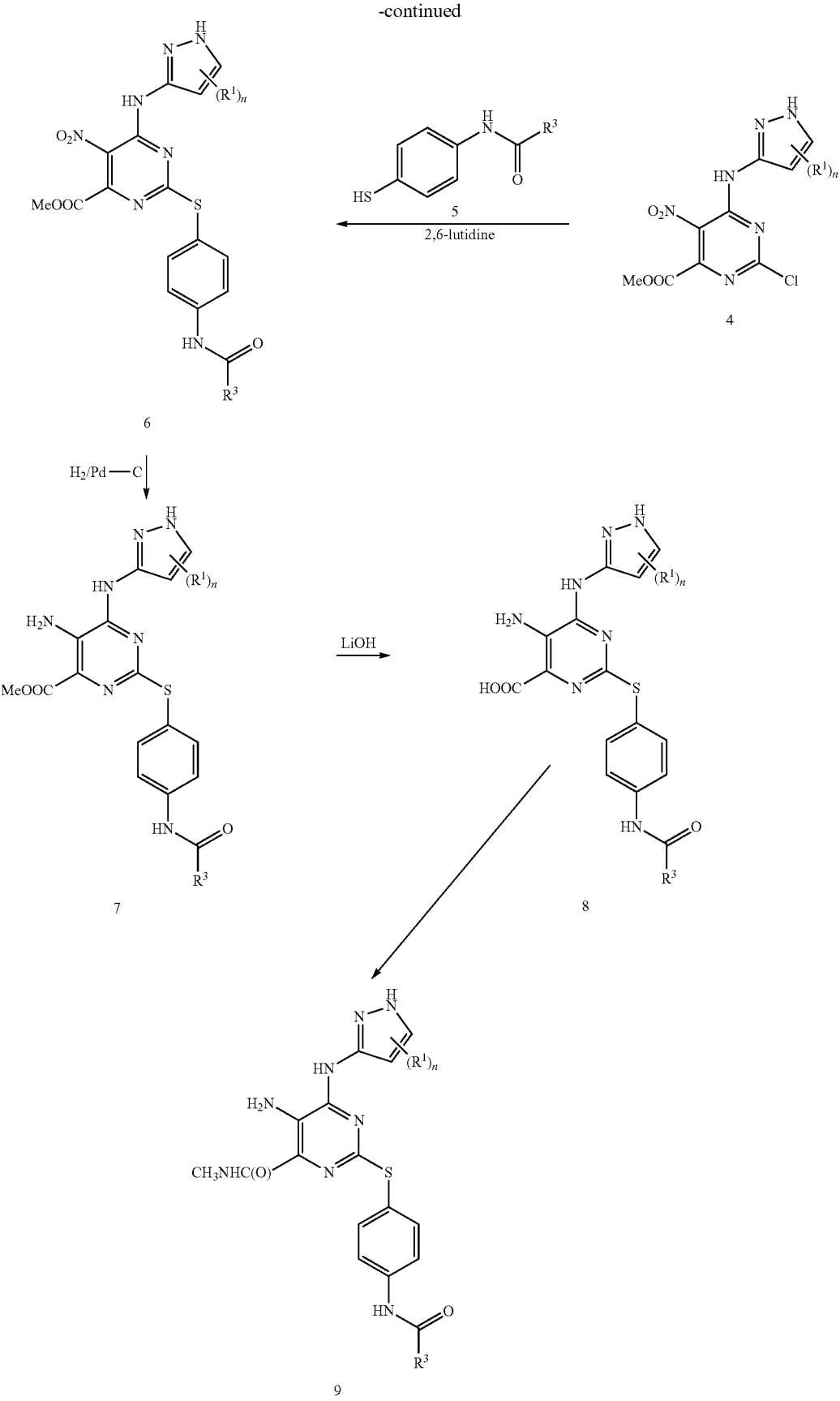

Specifically, in Scheme 1, methyl 5-nitroorotate, compound 2, is prepared from commercially available (Aldrich Chemical Company, Milwaukee, Wis., USA) potassium salt of 5-nitoorotic acid, compound 1, by conventional esterification techniques. Compound 2 may be isolated and purified using standard techniques such as chromatography, precipitation, crystallization, filtration, evaporation and the like. Alternatively, compound 2 may be isolated and used in the next step without further purification and/or isolation.

Conversion of compound 2 to the corresponding methyl 2,6-dichloro-5-nitro-4-pyrimidinecarboxylate, compound 3, proceeds by contacting compound 2 with an excess of $POCl_3$ in the presence of a suitable base to scavenge any acid generated. The reaction is typically conducted from room temperature to reflux and is generally complete within about 0.5 to 3 hours. Compound 3 may be isolated and purified using standard techniques such as chromatography, precipitation, crystallization, filtration, evaporation and the like. Alternatively, compound 3 may be isolated and used in the next step without purification and/or isolation.

Compound 3 is converted to methyl 2-(4-$R^3$-carboxamidophenylsulfanyl)-5-nitro-6-[$(R^1)_n$-pyrazol-3-ylamino]-4-pyrimidinecarboxylate, compound 6, in a two step process. Initially, a slight excess of 3-amino-$(R^1)_n$-pyrazole, typically greater than 1 to about 1.1 equivalents, is combined with compound 3 in an inert solvent such as dioxane, tetrahydrofuran, and the like. The reaction is preferably conducted in the presence of an excess of a suitable base such as 2,6-lutidine to scavenge the acid generated. The reaction is typically conducted at ambient temperatures and continued until the reaction is substantially complete which typically occurs within about 0.1 to 2 hours.

In the second step, the resulting methyl 2-chloro-5-nitro-6-[$(R^1)_n$-pyrazol-3-ylamino]-4-pyrimidinecarboxylate, compound 4, is not isolated. Rather, a slight excess (typically 1.1 to 1.3 equivalents) of 4-$R^3$-caboxamidothiophenol, compound 5 is added to the reaction mixture. Sufficient amounts of base are maintained in the reaction mixture to ensure that the acid generated by conversion to compound 6 is scavenged. The reaction typically is conducted at room temperature for a period of from about 2 to 24 hours. Compound 6 may be isolated and purified using standard techniques such as chromatography, precipitation, crystallization, filtration, evaporation and the like.

Compound 6 is converted to methyl 2-(4-$R^3$-carboxamidophenysulfanyl)-5-amino-6-[$(R^1)_n$-pyrazol-3-ylamino]-4-pyrimidinecarboxylate, compound 7, under conventional hydrogenation conditions. Compound 7, a compound of this invention, can be isolated and purified using standard techniques such as chromatography, precipitation, crystallization, filtration, evaporation and the like.

Alternatively, compound 7 can be used as an intermediate to provide for further compounds of this invention. In one embodiment, conventional hydrolysis of the methyl ester in compound 7 provides for 2-(4-$R^3$-carboxamidophenyl-sulfanyl)-5-amino-6-[$(R^1)_n$-pyrazol-3-ylamino]-4-pyrimidencarboxylic acid, compound 8.

Still further, compound 7 can be employed to prepare other carboxylate esters using conventional transesterification techniques as shown in Scheme 1A, wherein $R^a$ is alkyl, substituted alkyl, cycloalkyl, substituted cycloalkyl, heterocyclyl or substituted heterocyclyl. Such techniques include treating ester 7A with about 10 to 500 equivalents of an alcohol in the presence of about 0.2 to ten equivalents of titanium tetraisopropoxide or potassium cyanide at about 30 to 150° C. for about one to 72 hours to give esters 7B.

Scheme 1A

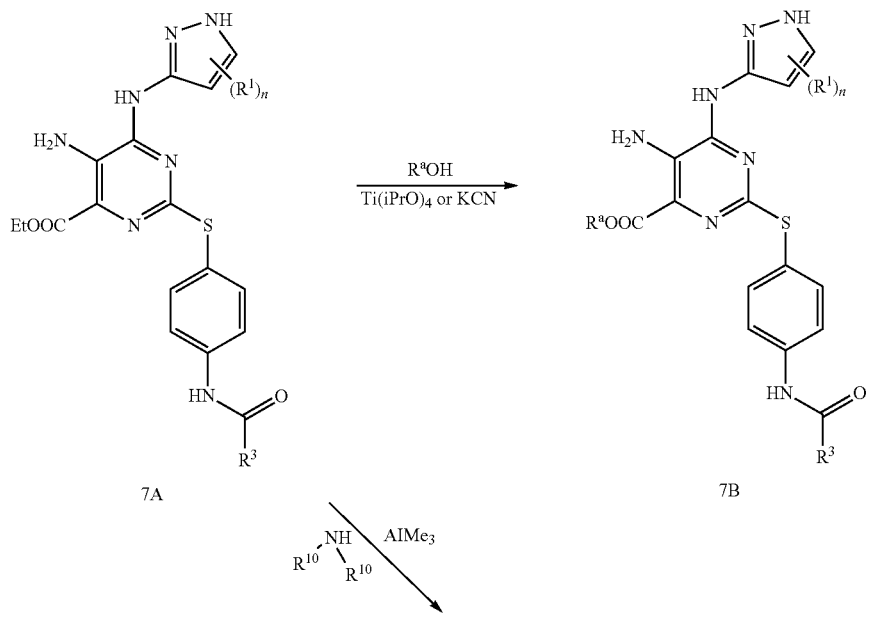

-continued

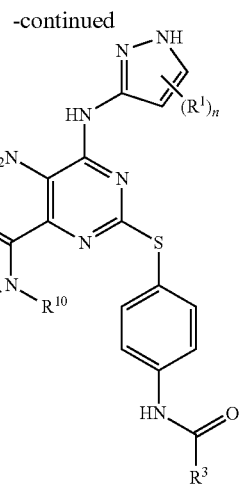

8B

Compound 8 can likewise be used as an intermediate in the preparation of 4-carboxamidopyrimidines 9 in Scheme 1 by amidation of the carboxyl group using conventional coupling reactions. Coupling reactions are conducted using well-known coupling reagents such as carbodiimides, BOP reagent (benzotriazol-1-yloxy-tris(dimethylamino)phosphonium hexafluorophosphonate) and the like. Suitable carbodiimides include, by way of example, dicyclohexylcarbodiimide (DCC), 1-(3-dimethylamino-propyl)-3-ethylcarbodiimide (EDC) and the like. If desired, polymer supported forms of carbodiimide coupling reagents may also be used including, for example, those described in Tetrahedron Letters, 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting compound 8 with about 1 to about 2 equivalents of the coupling reagent and at least one equivalent, preferably about 1 to about 1.2 equivalents, of a suitable amine in an inert diluent, such as dichloromethane, chloroform, acetonitrile, tetrahydrofuran, N,N-dimethylfomamide and the like. Generally, this reaction is conducted at a temperature ranging from about to about 0° to about 40° C. for about 2 to about 24 hours. Upon completion of the reaction, the carboxamido-pyrimidine derivative 9 is recovered by conventional methods including neutralization, extraction, precipitation, chromatography, filtration, and the like.

Alternatively, the 4-carboxamidopyrimidines of this invention can be prepared directly from ester 7 as shown in Scheme 1A, wherein $R^{10}$ is defined as above. For example, ester 7A is treated with about one to 10 equivalents of trimethylaluminum in a suitable solvent such as dichloromethane at about 0 to 30° C. for one minute to 60 minutes, about one to five equivalents of a primary or secondary amine is added, and the mixture is stirred at 0 to 35° C. for about one to 72 hours to give amides 8B. Under other reaction conditions, the trimethylaluminum is first added to the primary or secondary amine followed by the addition of the ester 7A.

Compound 5 and related compounds are prepared by conventional methods. Specifically, commercially available 4-amino-thiophenol (available from Aldrich Chemical Company, Milwaukee, Wis., USA as are the corresponding 3-aminothiophenol and 2-aminothiophenol) is reacted with an acid chloride of the formula $ClC(O)R^3$ under conventional amidation conditions including the use of a suitable base to scavenge the acid generated during reaction.

As noted above, the compounds depicted in Scheme 1 above employ a sulfur atom as Y. When so employed, such sulfur atoms can be oxidized to provide a sulfoxide or sulfone compound using conventional reagents and reaction conditions. Suitable reagents for oxidizing a sulfide compound to a sulfoxide include, by way of example, hydrogen peroxide, 3-chloroperoxybenzoic acid (MCPBA), sodium periodate, potassium peroxymonosulfate (OXONE®), and the like. The oxidation reaction is typically conducted by contacting the sulfide compound with about 0.95 to about 1.1 equivalents of the oxidizing reagent in an inert diluent, such as dichloromethane, at a temperature ranging from about −50° C. to about 75° C. for about 1 to about 24 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent. Such reactions are described further in March, "Advanced Organic Chemistry", 4th Ed., pp. 1202-1202, Wiley Publishers, (1992).

Compounds of this invention where Y is oxygen are prepared in a manner similar to that described above with the exception that the aminothiophenol is replaced with a 2-, 3-, or 4-aminophenol; each of which are commercially available Aldrich Chemical Company, Milwaukee, Wis., USA.

Similarly, compounds of this invention where Y is —NR— are prepared in a manner similar to that described above with the exception that an amino substituted aniline is employed in place of the aminothiophenol. 2-, 3- and 4-amino substituted anilines are similarly commercially available from Aldrich Chemical Company, Milwaukee, Wis., USA. When non-symmetric diamines are employed, it may be necessary to block one of the amino groups using conventional blocking groups to effect reaction at the desired amino group. Such methods are well within the skill of the artisan.

Compounds of this invention where W is a substituted amino group can be prepared by first blocking the amino groups of compound 6 using blocking groups which are orthogonal to removal by hydrogenation conditions. Next, the nitro group is then converted to an amino group in the manner described above. The amino group is then derivatized using conventional conditions to provide for a substituted amino group. Removal of the amino blocking groups then provides for a compound of this invention having a substituted amino group at the 5-position of the pyrimidine.

Compounds of this invention where Ar is heteroaryl are prepared as described above by use of a starting material of the formula: HY-Het-NH$_2$ where Y is as defined above and Het is either heteroaryl or substituted heteroaryl. Such compounds are either known in the art, some of which are commercially available or can be prepared by methods well known in the art.

Optionally substituted 3-amino substituted pyrazoles used in Scheme 1 above are known compounds some of which are commercially available or can be prepared by methods well known in the art. For example, 3-aminopyrazole, 3-amino-5-methylpyrazole, 3-amino-5-phenylpyrazole, and 3-amino-4-pyrazole carboxylic acid, are all commercially available from Adrich Chemical Company, Milwaukee, Wis., USA.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of this invention associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh. Alternatively, poorly water soluble compounds can be prepared in the form of nanoparticles to enhance their solubility. See, for example, International Patent Application Publication No. WO 03/024424 for "Stabilization of Active Agents by Formulation into Nanoparticulate Form" which is incorporated herein by reference in its entirety.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The compounds of the present invention maybe administered to patients either alone or in combination with other known anti-tumor agents. When administered alone, about 0.005 to about 100 mg/kg, more preferably about 0.005 to about 10 mg/kg, are administered to the patient. Higher and lower dosages may be used. Administration may occur once a day, or several times in a day. In addition the treatment may be repeated every 7, 14, 21 or 28 days.

When administered in combination with other anti-cancer agents, the compounds of the present invention may be prepared in a formulation that includes both one or more of the compounds of this invention and one or more other anti-cancer agents. Alternatively the other anti-cancer agents may be administered in a separate formulation which may be administered before, after or simultaneously with the compounds of this invention. When administered in combination with at least one other anti-cancer agent, about 0.005 to about 100 mg/kg, more preferably about 0.5 to about 10 mg/kg, of one or more compounds of this invention are administered to the patient. Higher and lower dosages may be used. The dosages of the other anti-cancer agents are known in the art. Administration may occur once a day, or several times in a day. In addition the treatment may be repeated every 7, 14, 21 or 28 days.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of this invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Lactose | 5 |
| Active Ingredient | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) | 50.0 mg |
| Microcrystalline cellulose (89%) | |
| Sucrose | 1.75 g |
| Sodium benzoate | 10.0 mg |
| Flavor and Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

FORMULATION EXAMPLE 9

An intravenous formulation may be prepared as follows:

| Ingredient | Quantity |
| --- | --- |
| Active Ingredient | 250.0 mg |
| Isotonic saline | 1000 mL |

FORMULATION EXAMPLE 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intraarterial infusion of hypertonic solutions which can transiently open the blood-brain barrier.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

atm=atmospheres
ATP=adenosine triphosphate
br s=broad singlet
C=growth control
° C.=degrees Celsius
$CDCl_3$=deuterated chloroform
d=doublet
DCC=N,N-dicyclohexylcarbodiimide
DCM=dichloromethane
DIEA=diisopropylethylamine
DMEM=Dulbeco's Modified Eagle's Medium
DMF=N,N-dimethylformamide
DMSO=dimethylsulfoxide
EDC=1-(3dimethylamino-propyl)-3-ethylcarbodiimide
EDTA=ethylenediamine tetraacetic acid
EGTA=ethylene glycolbis-(beta-aminoethylether))-N,N'-tetraacetic acid
equiv=equivalent
Em.=emission
EtOAc=ethyl acetate
$Et_3N$=triethyl amine
Ex.=excitation (or Example, depending on context)
DTT=dithiothreitol
g=grams
GI50=concentration of drug resulting in a 50% growth inhibition
h=hour
hrs.=hours
HEPES=N-(2-hydroxyethyl)piperazine-N'-(2-ethane-sulfonic acid
HOBt=1-hydroxybenzotriazole
HPLC=high performance liquid chromatography
IC50=concentration of drug resulting in a 50% inhibition
L=liter
LC50=concentration of drug resulting in a 50% reduction in the measured protein
m=multiplet
M=molar
Me=methyl
m/e=mass-to-charge ratio
MeOH=methanol
min=minutes
mg=milligram
mL or ml=milliliter
mm=millimeter
mM=millimolar
mol=mole
mmol=millimole
MHz=megahertz
MS=mass spectroscopy
N=normal
nm=nanometers
NMR=nuclear magnetic resonance
Pd/C=palladium on carbon
q=quartet
q.v.=adding a quantity sufficient to achieve a certain state
rt=room temperature
$R_f$=relative migration
s=singlet
sec=seconds
SRB=Sulphorhodamine-B
t=triplet
TCA=trichloroacetic acid
TFA=trifluoroacetic acid
THF=tetrahydrofuran
Ti=growth in the presence of drug
TLC or tlc=thin layer chromatography
Tris or Tris-HCl=tris(hydroxymethyl)aminomethane hydrochloride
Tz=time zero
w/v=weight to volume
v/v=volume to volume
μL or μl=microliter
μM=micromolar All the chemical starting materials were obtained from commercial suppliers and used without further purification.

Scheme 2 below illustrates reactions used in Examples 1-3.

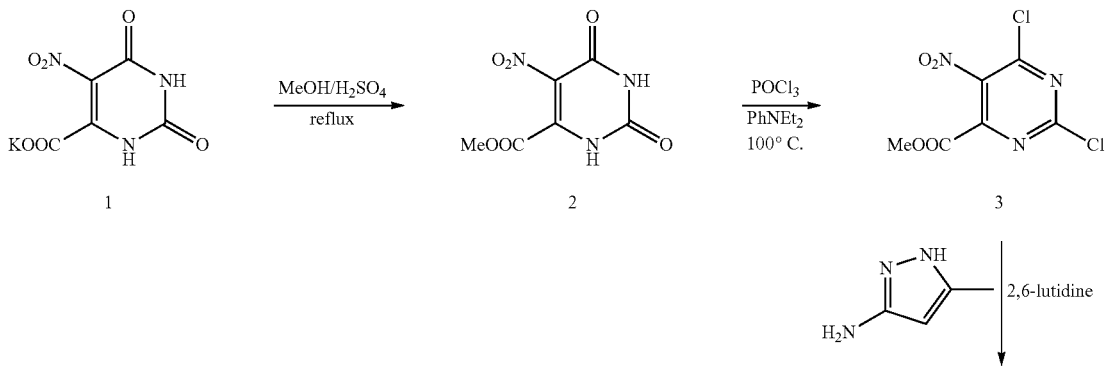

Scheme 2

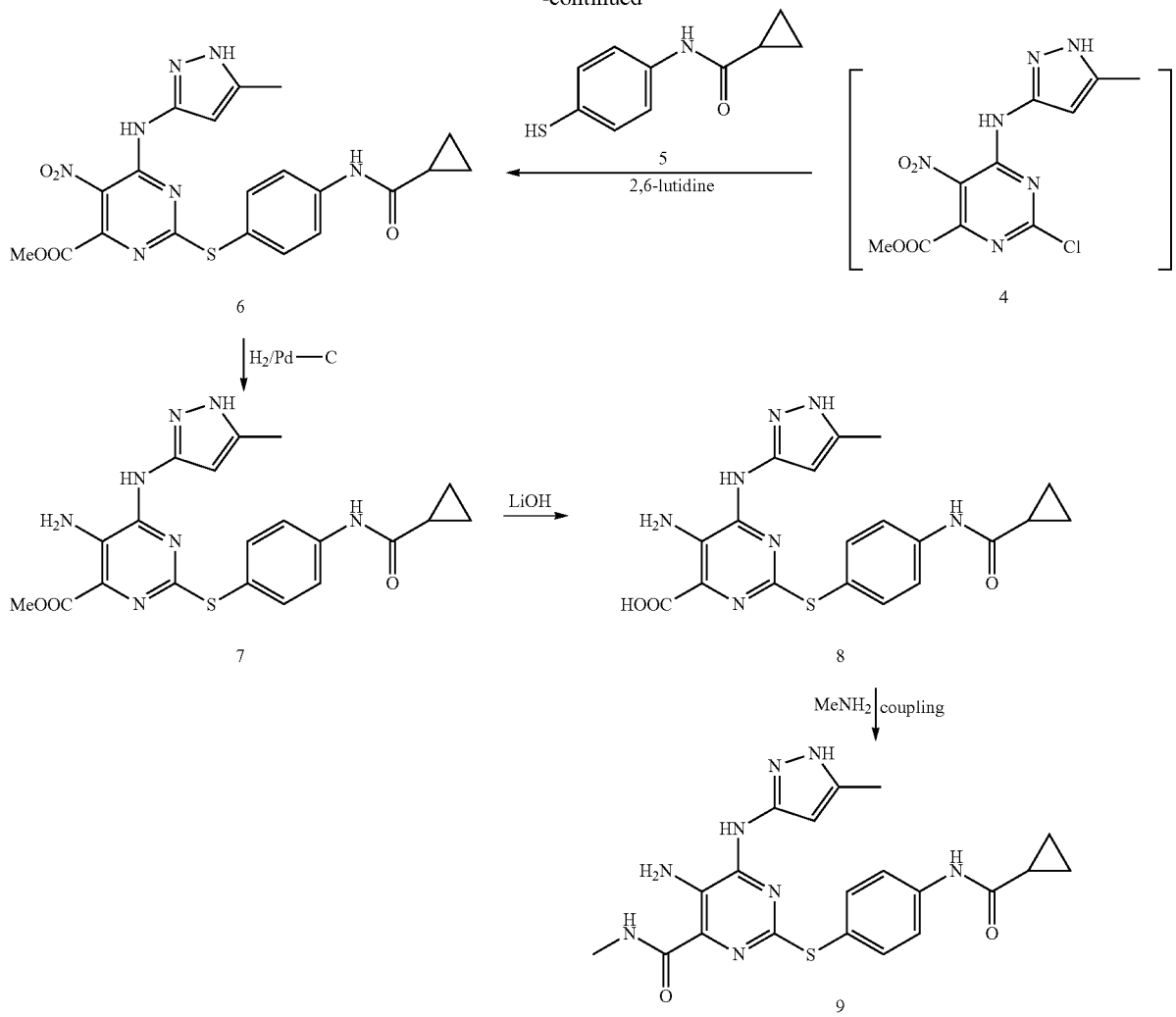

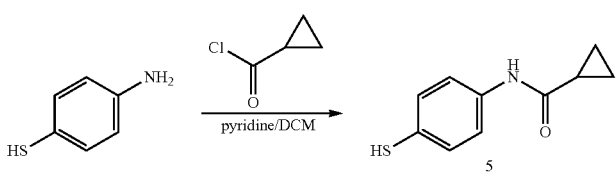

Preparation of 5:

Example 1

Preparation of Methyl 2-(4-cyclopropanecarboxamidophenylsulfanyl)-5-amino-6-(5-methylpyrazol-3-ylamino)-4-pyrimidinecarboxylate (Compound 7)

A. Preparation of Methyl 5-Nitroorotate (compound 2)

The potassium salt of 5-nitroorotic acid (25.0 g, 0.1 mol) was dissolved in MeOH (75 ml). Concentrated $H_2SO_4$ (21 mL) was added drop wise. The reaction was refluxed for 12 hrs. After cooling to room temperature, the white precipitate was collected by filtration, washed with water (50 mL×4), and dried under vacuum for 48 hrs. to afford compound 2 as a white power (26.0 g, 75%).

$R_f$ 0.10 (10% MeOH/DCM);
$^1$H NMR (300 MHz, DMSO-$d_6$) δ 11.90 (br s, 2 H), 3.8 (s, 3 H);
MS (electrospray) m/e 216 ($C_6H_5N_3O_6$+H).

B. Preparation of Methyl 2,6-dichloro-5-nitro-4-pyrimidine carboxylate (compound 3)

Compound 2 (1.00 g, 3.97 mmol) was dissolved in $POCl_3$ (4 mL). Diethylaniline (1.3 mL) was added drop wise at room temperature. The solution was stirred at room temperature for 30 min and then refluxed for 20 min. The mixture was concentrated under reduced pressure. The resulting oily residue was slowly poured onto a mixture of ice and water (10 mL). The mixture was extracted with ethyl acetate (20 mL×2). The combined organic solution was washed with 0.5 M HCl (10 mL), saturated $NaHCO_3$ (10 mL), and brine (10 mL). Drying over Na$_2$SO$_4$ and concentration under reduced pressure afforded a yellow oil (0.78 g, 78%).

MS (electrospray) m/e 252 (C$_6$H$_3$Cl$_2$N$_3$O$_4$+H).

C. Preparation of 4-Cyclopropanecarboxamidothiophenol (compound 5)

To 4-aminothiophenol (9.4 g, 75.0 mmol, 1.5 equiv) and pyridine (8.09 mL, 100.0 mmol, 2 equiv) at 0° C. was added cyclopropanecarbonyl chloride (4.58 mL, 50.0 mmol, 1 equiv) drop wise. The reaction was stirred from 0° C. to room temperature for overnight, diluted with EtOAc (200 mL), washed with 1 N HCl (50 mL×4), dried over Na$_2$SO$_4$, concentrated, and dried under vacuum to yield the compound 5 as a off-white solid (8.5 g, 88%).

R$_f$ 0.50 (50% EtOAc/hexane);
$^1$H NMR (300 MHz, DMSO-d$_6$) δ 10.10 (s, 1 H), 7.55 (d, J=5.8 Hz, 2 H), 7.30 (d, J=5.8 Hz, 2 H), 5.22 (s, 1 H), 1.60-1.80 (m, 1 H), 0.70-0.90 (m, 4 H); MS (electrospray) m/e 194 (C$_{10}$H$_{11}$NOS+H).

D. Preparation of Methyl 2-(4-cyclopropanecarboxamido-phenylsulfanyl)-5-nitro-6-(5-methylpyrazol-3-ylamino)-4-pyrimidinecarboxylate (compound 6)

To compound 3 (1.00 g, 3.76 mmol, 1 equiv) and 2,6-lutidine (1.31 mL, 11.25 mmol, 3 equiv) in dioxane (5 mL) at room temperature was added 3-amino-5-methyl-pyrazol (0.38 g, 3.95 mmol, 1.05 equiv, in 5 mL dioxane) drop wise. After stirring at room temperature for 0.5 hr, 4-cyclopropanecarboxamido-thiophenol (0.87 g, 4.5 mmol, 1.2 equiv) was added. The reaction was stirred at room temperature for overnight. The mixture was diluted with ethyl acetate and washed with 1 N HCl (50 mL) and saturated NaHCO$_3$ (50 mL). The organic layer was dried over Na$_2$SO$_4$ and concentrated under reduced pressure, and purified by flash column chromatography to yield compound 6 as a yellow solid (1.2 g, 70%).

R$_f$ 0.3 (3% MeOH/DCM);
MS (electrospray) m/e 470 (C$_{20}$H$_{19}$N$_7$O$_5$S+H).

E. Preparation of Methyl 2-(4-cyclopropanecarboxamido-phenylsulfanyl)-5-amino-6-(5-methylpyrazol-3-ylamino)-4-pyrimidinecarboxylate (compound 7)

Compound 6 (1.00 g) was dissolved in MeOH (10 mL) at room temperature. Pd/C (Degusa type) (10%, w/w, 0.5 g) was carefully added to the solution. The mixture was purged with H$_2$ for 10 min and stirred under H$_2$ atmosphere (1 atm) at room temperature for overnight. The catalyst was filtrated off with celite and washed with MeOH (30 mL×3). The filtrate was concentrated and purified by flash column chromatography with 0%-6% MeOH/DCM to yield compound 7 as a yellow solid (0.94 g, 98%).

R$_f$ 0.3 (5% MeOH/DCM);
$^1$H NMR (300 MHz, CDCl$_3$) δ 11.91 (s, 1 H), 10.19 (s, 1 H), 9.52 (s, 1 H), 7.70 (d, J=8.4 Hz, 2 H), 7.47 (d, J=8.4 Hz, 2 H), 6.70 (s, 2 H), 5.38 (s, 1 H), 3.81 (s, 3 H), 1.96 (s, 3 H), 1.82 (m, 1 H), 0.81 (m, 4 H); MS (electrospray) m/e 440 (C$_{20}$H$_{21}$N$_7$O$_3$S+H).

Example 2

Preparation of 2-(4-Cyclopropanecarboxamidophenylsulfanyl)-5-amino-6-(5-methylpyrazol-3-ylamino)-4-pyrimidinecarboxylic acid (compound 8)

Compound 7 (45 mg, 0.1 mmol, 1 equiv) was dissolved in THF (1 mL). LiOH (1 mL, 0.4 N, 0.4 mmol, 4 equiv) was added to the solution. The mixture was stirred at room temperature for overnight, acidified to pH=5-6 with dilute HCl (1 N), concentrated under reduced pressure at room temperature, and dried under high vacuum for 48 hrs. to afford the crude product, which was used directly in the next step without further purification. A small sample was purified with reverse phase HPLC to afford the compound 8 as a white solid.

$^1$H NMR (300 MHz, DMSO-d$_6$) δ 10.48 (br s, 1 H), 10.40 (s, 2 H), 9.60 (s, 1 H), 7.71 (d, J=8.7 Hz, 2 H), 7.65 (br s, 1 H), 7.49 (d, J=8.1 Hz, 2 H), 5.35 (s, 1 H), 1.95 (s, 3 H), 1.80-1.90 (m, 1 H), 0.70-0.90 (m, 4 H);
MS (electrospray) m/e 426 (C$_{19}$H$_{19}$N$_7$O$_3$S+H).

Example 3

Preparation of Methyl 2-(4-cyclopropanecarboxamidophenylsulfanyl)-5-amino-6-(5-methylpyrazol-3-ylamino)-4-pyrimidinecarboxamide (compound 9)

To compound 8 (crude, ~0.12 mmol, 1 equiv) in DCM/DMF (10 mL, 1:1, v/v) was added DIEA (0.21 mL, 1.2 mmol, 10 equiv), MeNH$_2$ (0.12 mL, 2 N/THF, 0.24 mmol, 2 equiv), HOBt (92 mg, 0.60 mmol, 5 equiv), and EDC (115 mg, 0.60 mmol, 5 equiv) sequentially. The reaction was vigorously stirred at room temperature for overnight, diluted with EtOAc (50 mL), washed with saturated NaHCO$_3$ (20 mL×3), dried over Na$_2$SO$_4$, concentrated under reduced pressure, and purified on preparative TLC with 5% Et$_3$N/10% MeOH/DCM to yield the desired compound 9 as light-yellow solid (17 mg, 32% from ester).

R$_f$ 0.40 (5% Et$_3$N/10% MeOH/DCM);
MS (electrospray) m/e 439 (C$_{20}$H$_{22}$N$_8$O$_2$S+H).

Example 4

Preparation of Ethyl 2-(4-cyclopropanecarboxamidophenylsulfanyl)-5-amino-6-(5-methylpyrazol-3-ylamino)-4-pyrimidinecarboxylate (compound 11)

A. Preparation of Ethyl 2-(4-cyclopropanecarboxamido-phenylsulfanyl)-5-nitro-6-(5-methylpyrazol-3-ylamino)-4-pyrimidinecarboxylate (compound 10)

The title compound was prepared in the manner described above for the methyl ester starting from commercially available ethyl 2,6-dichloro-5-nitropyrimdinecarboxylate (Matrix Scientific, South Carolina) to provide for a yellow solid.

R$_f$ 0.35 (5% MeOH/DCM);
$^1$H NMR (300 MHz, CDCl$_3$) δ 10.55 (br s, 1 H), 8.68 (br s, 1 H), 7.82 (s, J=9.0 Hz, 2 H), 7.55 (d, J=9.0 Hz, 2 H), 7.50 (br s, 1 H), 5.62 (br s, 2 H), 4.51 (q, J=7.5 Hz, 2 H), 2.26 (s, 3 H), 1.68-1.78 (m, 1 H), 1.43 (t, J=7.3 Hz, 3 H), 1.08-1.16 (m, 2 H), 0.88-0.96 (m, 2 H);
MS (electrospray) m/e 484 (C$_{21}$H$_{21}$N$_7$O$_5$S+H).

B. Ethyl 2-(4-cyclopropanecarboxamidophenylsulfanyl)-5-amino-6-(5-methylpyrazol-3-ylamino)-4-pyrimidinecarboxylate (compound 11)

The title compound was prepared in the manner described above for the methyl ester to provide for a yellow solid.

R$_f$ 0.33 (10% MeOH/DCM);
$^1$H NMR (300 MHz, DMSO-d$_6$) δ 11.89 (s, 1 H), 10.38 (s, 1 H), 9.48 (s, 1 H), 7.80 (d, J=10.8 Hz, 2 H), 7.49 (d, J=10.7

Hz, 2 H), 6.71 (br s, 2 H), 5.34 (s, 1 H), 4.28 (q, J=8.1 Hz, 2 H), 1.95 (s, 3 H), 1.80-1.8 (m, 1 H), 1.25-1.38 (m, 2 H), 0.80-0.85 (m, 2 H);
MS (electrospray) m/e 454 ($C_{21}H_{23}N_7O_3S$+H).

Example 5

Preparation of N-[2-(N,N-dimethylamino)ethyl]-2-(4-cyclopropane-carboxamidophenylsulfanyl)-5-amino-6-(5-methylpyrazol-3-ylamino)-4-pyrimidine carboxamide (compound 12)

The title compound was prepared in the manner described above for compound 9 with the exception that the methylamine reagent was replaced with 2-(N,N-dimethylamino)ethylamine. The title compound was recovered as a yellow-off white solid.
$R_f$ 0.45 (10% Et$_3$N/10% MeOH/DCM);
MS (electrospray) m/e 496 ($C_{23}H_{29}N_9O_2S$+H).

Examples 6 and 7

Preparation of Ethyl 2-(4-cyclopropanecarboxamidophenylsulfonyl)-5-amino-6-(5-methylpyrazol-3-ylamino)-4-pyrimidinecarboxylate (compound 13)
and Preparation of ethyl 2-(4-cyclopropane-carboxamidophenylsulfinyl)-5-amino-6-(5-methylpyrazol-3-ylamino)-4-pyrimidinecarboxylate (compound 14)

To compound 11 (45 mg, 0.10 mmol, 1 equiv) in THF (3 mL) was added 0.1 M Oxone aqueous solution (1.1 mL, 0.11 mmol, 1.1 equiv) drop wise and water (2 mL) at room temperature. The clear solution was vigorously stirred at room temperature for overnight. Aqueous Na$_2$S$_2$O$_3$ (1 M, 5 mL) and saturated NaHCO$_3$ (5 mL) was added. The mixture was vigorously stirred at room temperature for 10 min, extracted with EtOAc (20 mL×5). The combined extracts were dried over Na$_2$SO$_4$, and concentrated under reduced pressure. The crude products were purified with preparative TLC with 10% MeOH/DCM to yield sulfone 13 and sulfoxide 14 as yellow solids.
Compound 13 (11 mg, 23%):
$R_f$ 0.50 (10% MeOH/DCM);
MS (electrospray) m/e 486 ($C_{21}H_{23}N_7O_5S$+H).
Compound 14 (22 mg, 47%)
$R_f$ 0.40 (10% MeOH/DCM);
MS (electrospray) m/e 470 ($C_{21}H_{23}N_7O_4S$+H).

Example 8

N-(2-Piperidin-1-ylethyl) 2-(4-cyclopropanecarboxamidophenylsulfanyl)-5-amino-6-(5-methylpyrazol-3-ylamino)-4-pyrimidinecarboxamide (Compound 17)

To a mixture of Compound 11 (250 mg, 0.55 mmol, 1 equiv) in dry CH$_2$Cl$_2$ at 0° C. was added trimethylaluminum (1.6 mL, 2 M/toluene, 3.2 mmol, 5.8 equiv) dropwise. After stirring for 5 min., 2-piperidin-1-ylethanamine (0.086 mL, 0.61 mmol, 1.1 equiv) was added and the reaction was stirred at rt for overnight under a nitrogen atmosphere. The reaction was quenched with 1.5 N HCl (10 mL) and the resultant solid was filtered off. The solid was washed with water and CH$_2$Cl$_2$. The crude material was then purified by column chromatography to yield the desired product 17 as a light-yellow solid (250 mg): $^1$H NMR (DMSO, 400 MHz) δ 11.95 (s, 1 H), 10.45 (s, 1 H), 9.39 (br s, 1 H), 8.29 (s, 1 H), 7.73 (d, J=8.4 Hz, 2 H), 7.50 (d, J=8.4 Hz, 2 H), 6.83 (s, 2 H), 5.48 (s, 1 H), 3.30-3.35 (m, 2 H), 2.37-2.50 (m, 6 H), 2.00 (s, 3 H), 1.81 (m, 1 H), 1.40-1.50 (m, 4 H), 1.39 (br s, 2 H), 0.81 (d, J=5.9 Hz, 4 H); MS (electrospray) m/e 536 ($C_{26}H_{33}N_9O_2S$+H).

Examples 9-27 were prepared in the same manner as Example 8 by substituting the appropriate amine for 2-piperidin-1-ylethanamine.

Example 9

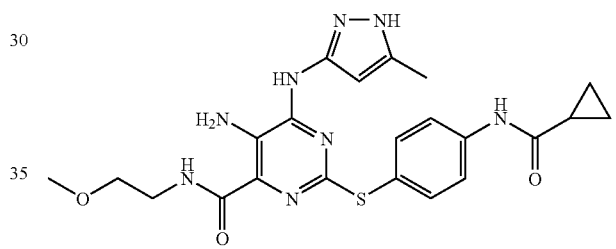

N-(2-Methoxyethyl) 2-(4-cyclopropanecarboxamidophenylsulfanyl)-5-amino-6-(5-methylpyrazol-3-ylamino)-4-pyrimidinecarboxamide (Compound 43)

From 2-methoxyethanamine and Compound 11 was obtained Example 9: $^1$H NMR (400 MHz, DMSO-d$_6$) δ11.96 (brs, 1 H), 10.43 (br s, 1 H), 9.41 (br s, 1 H), 8.27 (br s, 1 H), 7.72 (br s, 2 H), 7.50 (br s, 2 H), 6.82 (br s, 2 H), 5.47 (s, 1 H), 3.56 (br s, 2H), 3.40 (s, 3 H), 1.97 (s, 3 H), 1.79 (m, 1 H), 1.16 (br s, 2 H), 0.80 (br s, 4 H); MS (electrospray) m/e 483 ($C_{22}H_{26}N_8O_3S$+H).

Example 10

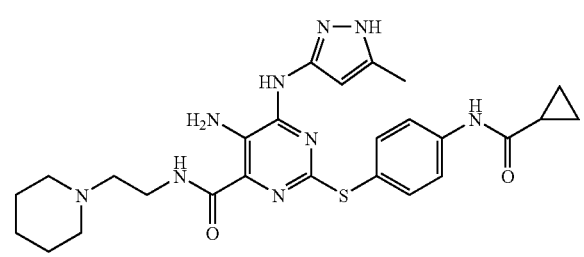

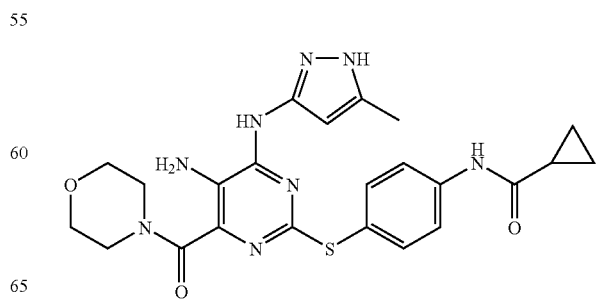

Morpholin-4-yl 2-(4-cyclopropanecarboxamidophenylsulfanyl)-5-amino-6-(5-methylpyrazol-3-ylamino)-4-pyrimidinecarboxamide (Compound 44)

From morpholine and Compound 11 was obtained Example 10: $^1$H NMR (400 MHz, DMSO-d$_6$) δ11.90 (s, 1 H), 10.43 (s, 1 H), 9.18 (s, 1 H), 7.71 (d, J=8.0 Hz, 2 H), 7.48 (d, J=8.0 Hz, 2 H), 5.76 (s, 1 H), 5.31 (s, 2 H), 3.58-3.64 (m, 4 H), 3.64 (br s, 2 H), 3.39 (br s, 2 H), 2.01 (s, 3 H), 1.82 (m, 1 H), 0.81 (d, J=4.0 Hz, 4 H); MS (electrospray) m/e 495 (C$_{23}$H$_{26}$N$_8$O$_3$S+H).

Example 11

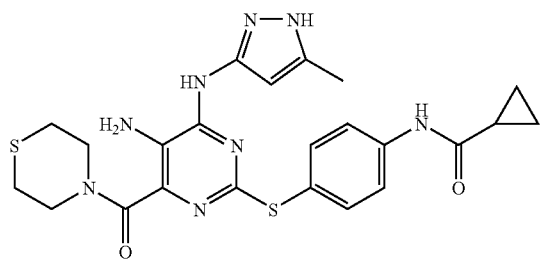

Thiomorpholin-4-yl 2-(4-cyclopropanecarboxamidophenylsulfanyl)-5-amino-6-(5-methylpyrazol-3-ylamino)-4-pyrimidinecarboxamide (Compound 45)

From morpholine and Compound 11 was obtained Example 11: $^1$H NMR (400 MHz, DMSO-d$_6$) δ11.88 (br s, 1 H), 10.42 (br s, 1 H), 9.16 (br s, 1 H), 7.71 (d, J=8.0 Hz, 2 H), 7.49 (d, J=8.0 Hz, 2 H), 5.46 (s, 1 H), 5.17 (br s, 2 H), 3.83 (br s, 2 H), 3.60 (br s, 2 H), 2.69 (br s, 2 H), 2.55 (br s, 2 H), 1.99 (s, 3 H), 1.81 (m, 1 H), 0.81 (d, J=4.0 Hz, 4 H); MS (electrospray) m/e 511 (C$_{23}$H$_{26}$N$_8$O$_2$S$_2$+H).

Example 12

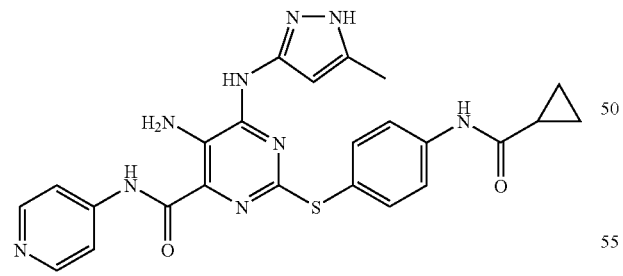

N-Pyridin-4-yl 2-(4-cyclopropanecarboxamidophenylsulfanyl)-5-amino-6-(5-methylpyrazol-3-ylamino)-4-pyrimidinecarboxamide (Compound 51)

From 4-aminopyridine and Compound 11 was obtained Example 12: $^1$H NMR (400 MHz, DMSO-d$_6$) δ12.05 (br s, 1 H), 10.52 (s, 1 H), 10.43 (s, 1 H), 9.72 (s, 1 H), 8.53 (br s, 2 H), 7.85 (br s, 2 H), 7.76 (br s, 2 H), 7.56 (br s, 2 H) 7.03 (s, 2 H), 5.64 (s, 1H), 2.05 (s, 3 H), 1.99 (m, 1 H), 0.84 (br s, 4 H); MS (electrospray) m/e 502 C$_{24}$H$_{23}$N$_9$O$_2$S+H).

Example 13

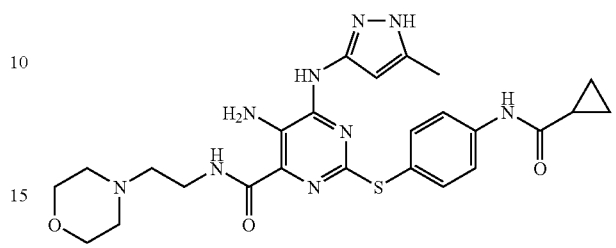

N-(2-Morpholin-4-ylethyl) 2-(4-cyclopropanecarboxamidophenylsulfanyl)-5-amino-6-(5-methylpyrazol-3-ylamino)-4-pyrimidinecarboxamide (Compound 52)

From 2-morpholin-4-ylethanamine and Compound 11 was obtained Example 13: $^1$H NMR (400 MHz, DMSO-d$_6$) δ11.95 (s, 1 H), 10.44 (s, 1 H), 9.41 (s, 1 H), 8.32 (s, 1H), 7.73 (d, J=8.2, 2H), 7.51 (d, J=8.2 Hz, 2 H), 6.84 (s, 2 H), 5.47 (s, 1 H), 3.58 (br s, 4 H), 3.31 (br s, 2 H), 2.41-2.51 (m, 6 H), 2.00 (s, 3 H), 1.82 (m, 1 H), 0.81 (d, J=5.4 Hz, 4 H); MS (electrospray) m/e 538 (C$_{25}$H$_{31}$N$_9$O$_3$S+H).

Example 14

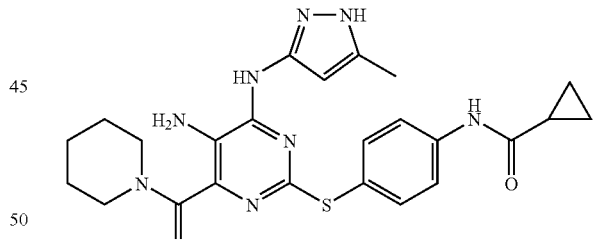

Piperidin-1-yl 2-(4-cyclopropanecarboxamidophenylsulfanyl)-5-amino-6-(5-methylpyrazol-3-ylamino)-4-pyrimidinecarboxamide (Compound 53)

From piperidine and Compound 11 was obtained Example 14: $^1$H NMR (400 MHz, DMSO-d$_6$) δ11.88 (s, 1 H), 10.43 (s, 1 H), 9.12 (s, 1 H), 7.71 (d, J=8.5 Hz, 2 H), 7.49 (d, J=8.5 Hz, 2 H), 5.45 (s, 1 H), 5.09 (s, 2 H), 3.51 (br s, 2 H), 3.23 (br s, 2 H), 1.97 (s, 3 H), 1.81 (m, 1 H), 1.57 (br s, 4 H), 1.43 (br s, 2 H), 0.81 (d, J=6.0 Hz, 4 H); MS (electrospray) m/e 493 ($C_{24}H_{28}N_8O_2S$+H).

H), 1.69-1.75 (m, 2 H), 0.81 (d, J=6.0 Hz, 4H); MS (electrospray) m/e 497 ($C_{23}H_{28}N_8O_3S$+H).

Example 15

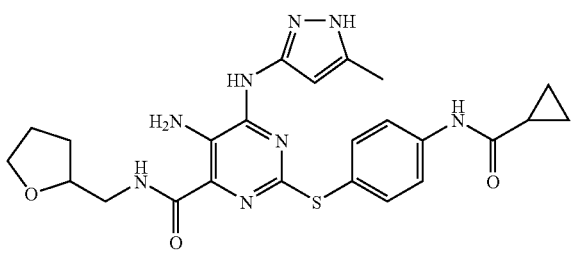

N-(Tetrahydrofuran-2-ylmethyl) 2-(4-cyclopropanecarboxamidophenylsulfanyl)-5-amino-6-(5-methylpyrazol-3-ylamino)-4-pyrimidinecarboxamide (Compound 54)

From 1-tetrahydrofuran-2-ylmethanamine and Compound 11 was obtained Example 15: $^1$H NMR (400 MHz, DMSO-$d_6$) δ10.50 (s, 1 H), 9.63 (s, 1 H), 8.20 (s, 1 H), 7.75 (d, J=8.2 Hz, 2 H), 7.51 (d, J=8.2 Hz, 2 H), 5.57 (s, 1 H), 3.92 (t, J=5.7 Hz, 1 H), 3.75 (d, J=6.9 Hz, 1 H), 3.63 (d, J=7.1 Hz, 1 H), 3.24-3.33 (m, 2 H), 2.03 (s, 3 H), 1.81-1.86 (m, 4 H), 1.49-1.53 (m, 1 H), 0.82 (d, J=5.7 Hz, 4 H); MS (electrospray) m/e 509 ($C_{24}H_{28}N_8O_3S$+H).

Example 16

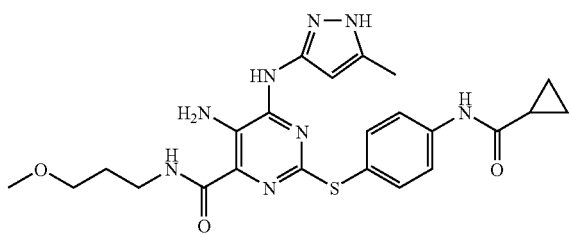

N-(3-Methoxypropyl) 2-(4-cyclopropanecarboxamidophenylsulfanyl)-5-amino-6-(5-methylpyrazol-3-ylamino)-4-pyrimidinecarboxamide (Compound 55)

From 3-methoxypropanamine and Compound 11 was obtained Example 16: $^1$H NMR (400 MHz, DMSO-$d_6$) δ10.49 (s, 1 H), 9.54 (s, 1 H), 8.38 (t, J=5.9 Hz, 1 H), 7.75 (d, J=8.5 Hz, 2 H), 7.51 (d, J=8.5 Hz, 2 H), 5.49 (s, 1 H), 3.35 (t, J=6.1 Hz, 2 H), 3.25-3.30 (m, 5 H), 2.01 (s, 3 H), 1.85 (m, 1

Example 17

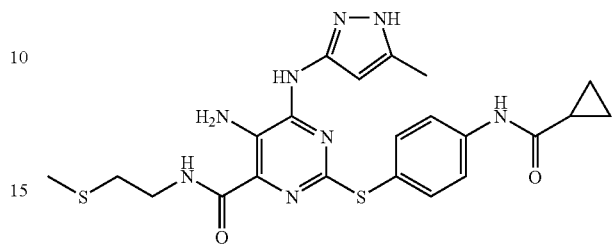

N-(2-Methylthioethyl) 2-(4-cyclopropanecarboxamidophenylsulfanyl)-5-amino-6-(5-methylpyrazol-3-ylamino)-4-pyrimidinecarboxamide (Compound 56)

From 2-(methylthio)ethanamine and Compound 11 was obtained Example 17: $^1$H NMR (400 MHz, DMSO-$d_6$) δ10.50 (s, 1 H), 9.58 (s, 1 H), 8.49 (s, 1 H), 7.75 (d, J=7.9 Hz, 2 H), 7.51 (d, J=7.9 Hz, 2 H), 5.46 (s, 1 H), 3.42 (t, J=6.4 Hz, 2 H), 2.62 (t, J=6.4 Hz, 2 H), 2.09 (s, 3 H), 2.00 (s, 3 H), 1.84 (m, 1 H), 0.81 (d, J=5.3 Hz, 4 H); MS (electrospray) m/e 499 ($C_{22}H_{26}N_8O_2S_2$+H).

Example 18

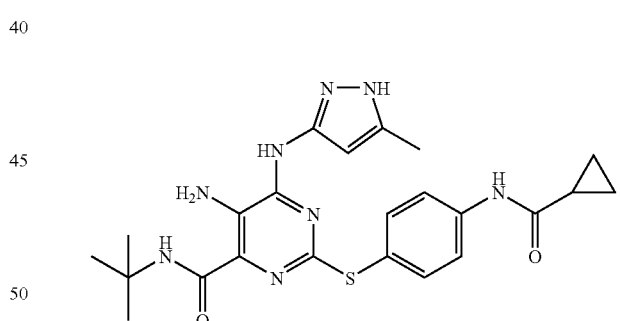

N-(tert-Butyl) 2-(4-cyclopropanecarboxamidophenylsulfanyl)-5-amino-6-(5-methylpyrazol-3-ylamino)-4-pyrimidinecarboxamide (Compound 57)

From tert-butylamine and Compound 11 was obtained Example 18: $^1$H NMR (400 MHz, DMSO-$d_6$) δ12.02 (s, 1 H), 10.41 (s, 1 H), 9.43 (s, 1 H), 7.73 (d, J=8.6 Hz, 2H), 7.65 (s, 1 H), 7.50 (d, J=8.6 Hz, 2 H), 6.83 (s, 2 H), 5.86 (s, 1 H), 2.09

(s, 3 H), 1.81 (m, 1 H), 1.29 (s, 9 H), 0.81 (d, J=6.2 Hz, 4 H); MS (electrospray) m/e 481 ($C_{23}H_{28}N_8O_2S$+H).

Example 19

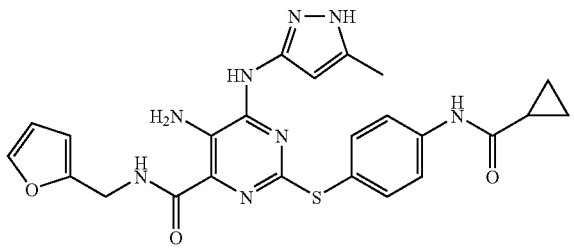

N-(2-Furylmethyl) 2-(4-cyclopropanecarboxamidophenylsulfanyl)-5-amino-6-(5-methylpyrazol-3-ylamino)-4-pyrimidinecarboxamide (Compound 58)

From 1-(2-furyl)methanamine and Compound 11 was obtained Example 19: $^1$H NMR (400 MHz, DMSO-$d_6$) δ10.44 (s, 1 H), 9.45 (s, 1 H), 8.67 (s, 1 H), 7.73 (d, J=7.5 Hz, 2 H), 7.58 (s, 1 H), 7.50 (d, J=7.5 Hz, 2 H), 6.40 (s, 1 H), 6.25 (s, 1 H), 5.43 (s, 1 H), 4.42 (d, J=4.0 Hz, 2 H), 1.99 (s, 3 H), 1.83 (br s, 1 H), 0.82 (d, J=4.3 Hz, 4 H); MS (electrospray) m/e 505 ($C_{24}H_{24}N_8O_3S$+H).

Example 20

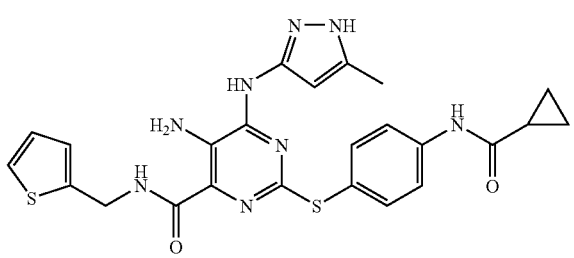

N-(2-Thien-2-ylmethyl) 2-(4-cyclopropanecarboxamidophenylsulfanyl)-5-amino-6-(5-methylpyrazol-3-ylamino)-4-pyrimidinecarboxamide (Compound 59)

From 1-thien-2-ylmethanamine and Compound 11 was obtained Example 20: $^1$H NMR (400 MHz, DMSO-$d_6$) δ10.52 (s, 1 H), 9.69 (s, 1 H), 8.90 (t, J=6.1 Hz, 1 H), 7.74 (d, J=8.4 Hz, 2 H), 7.50 (d, J=8.4 Hz, 2 H), 7.39 (d, J=4.9 Hz, 1 H), 6.96-7.01 (m, 2H), 5.49 (s, 2 H), 4.58 (d, J=6.1 Hz, 2 H), 1.98 (s, 3 H), 1.85 (m, 1 H), 0.82 (d, J=6.0 Hz, 4 H); MS (electrospray) m/e 521 ($C_{24}H_{24}N_8O_2S_2$+H).

Example 21

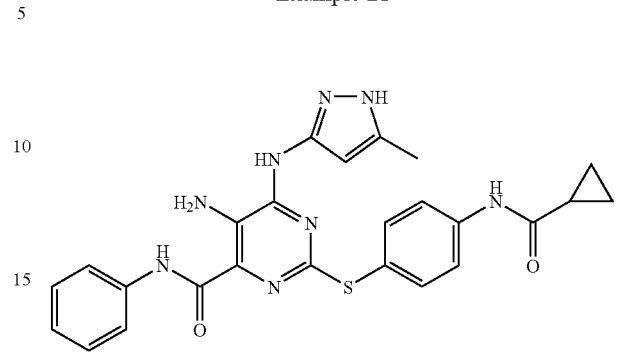

N-Phenyl 2-(4-cyclopropanecarboxamidophenylsulfanyl)-5-amino-6-(5-methylpyrazol-3-ylamino)-4-pyrimidinecarboxamide (Compound 60)

From aniline and compound 11 was obtained Example 21: $^1$H NMR (400 MHz, DMSO-$d_6$) δ12.05 (s, 1 H), 10.49 (s, 1 H), 9.83 (s, 1 H), 9.60 (s, 1 H), 7.79 (d, J=8.1 Hz, 2 H), 7.57-7.60 (m, 4 H), 7.33 (t, J=7.4 Hz, 2 H), 7.11 (t, J=7.1 Hz, 1 H), 6.93 (s, 2H), 5.87 (s, 1 H), 2.11 (s, 3 H), 1.85 (m, 1 H), 0.85 (d, J=5.4 Hz, 4 H); MS (electrospray) m/e 501 ($C_{25}H_{24}N_8O_2S$+H).

Example 22

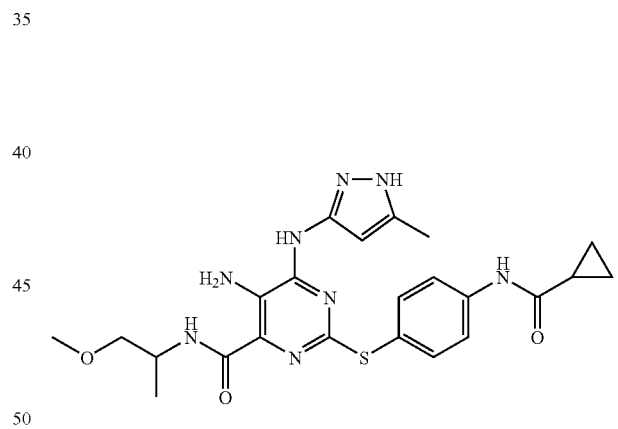

N-(2-Methoxy-1-methylethyl) 2-(4-cyclopropanecarboxamidophenylsulfanyl)-5-amino-6-(5-methylpyrazol-3-ylamino)-4-pyrimidinecarboxamide (Compound 61)

From 1-methoxypropane-2-amine and Compound 11 was obtained Example 22: $^1$H NMR (400 MHz, DMSO-$d_6$) δ10.43 (s, 1 H), 9.43 (s, 1 H), 7.94 (d, J=8.7 Hz, 1 H), 7.74 (d, J=8.6 Hz, 2 H), 7.51 (d, J=8.6 Hz, 2 H), 5.61 (s, 1 H), 4.08 (m, 1 H), 3.29-3.37 (m, 2 H), 3.27 (s, 3 H), 2.03 (s, 3 H), 1.75 (m, 1 H), 1.10 (d, J=6.7 Hz, 3 H), 0.82 (d, J=6.2 Hz, 4 H); MS (electrospray) m/e 497 ($C_{23}H_{28}N_8O_3S$+H).

Example 23

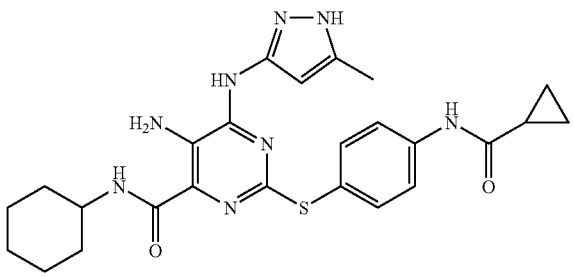

N-Cyclohexyl 2-(4-cyclopropanecarboxamidophenylsulfanyl)-5-amino-6-(5-methylpyrazol-3-ylamino)-4-pyrimidinecarboxamide (Compound 62)

From cyclohexylamine and Compound 11 was obtained Example 23: $^1$H NMR (400 MHz, DMSO-$d_6$) δ12.03 (br s, 1 H), 10.45 (s, 1 H), 9.44 (s, 1 H), 7.71-7.76 (m, 3H), 7.50 (d, J=7.8 Hz, 2 H), 6.79 (s, 1 H), 5.86 (s, 1 H), 2.09 (s, 3 H), 1.82 (m, 1 H), 1.54-1.71 (m, 4 H), 1.15-1.31 (m, 6 H), 0.82 (d, J=5.3 Hz, 4 H); MS (electrospray) m/e 507 ($C_{25}H_{30}N_8O_2S$+H).

Example 24

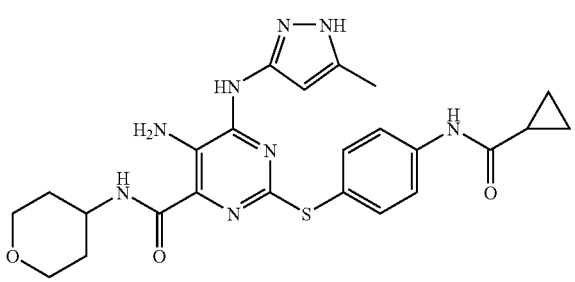

N-Tetrahydro-2H-pyran-4-yl 2-(4-cyclopropanecarboxamidophenylsulfanyl)-5-amino-6-(5-methylpyrazol-3-ylamino)-4-pyrimidinecarboxamide (Compound 63)

From tetrahydro-2H-pyran-4-amine and Compound 11 was obtained Example 24: $^1$H NMR (400 MHz, DMSO-$d_6$) δ11.99 (s, 1 H), 10.44 (s, 1 H), 9.43 (s, 1 H), 7.94 (m, 1 H), 7.93 (d, J=8.5 Hz, 2 H), 7.51 (d, J=8.5 Hz, 2 H), 6.82 (s, 2 H), 5.69 (s, 1 H), 3.79-3.88 (m, 3 H), 3.32-3.40 (m, 2H), 2.05 (s, 3 H), 1.69-1.84 (m, 3 H), 1.48-1.51 (m, 2 H), 0.82 (d, J=6.0 Hz, 4 H); MS (electrospray) m/e 509 ($C_{24}H_{28}N_8O_3S$+H).

Example 25

N-(1-Methylpiperidin-4-yl) 2-(4-cyclopropanecarboxamidophenylsulfanyl)-5-amino-6-(5-methylpyrazol-3-ylamino)-4-pyrimidinecarboxamide (Compound 64)

From 1-methylpiperidine-4-amine and Compound 11 was obtained Example 25: $^1$H NMR (400 MHz, DMSO-$d_6$) δ12.00 (br s, 1 H), 10.48 (s, 1 H), 9.44 (s, 1 H), 7.93 (d, 1 H), 7.75 (d, 2H, J=8.5 Hz, 2 H), 7.50 (d, J=8.5 Hz, 2 H), 6.81 (s, 2 H), 5.68 (s, 1 H), 3.34 (br s, 1 H), 2.81 (br s, 2 H), 2.52-2.55 (m, 5 H), 2.32 (s, 3 H), 1.76-1.85 (m, 3 H), 1.59-1.56 (m, 2 H), 0.82 (d, J=6.2 Hz, 4 H); MS (electrospray) m/e 522 ($C_{25}H_{31}N_9O_2S$+H).

Example 26

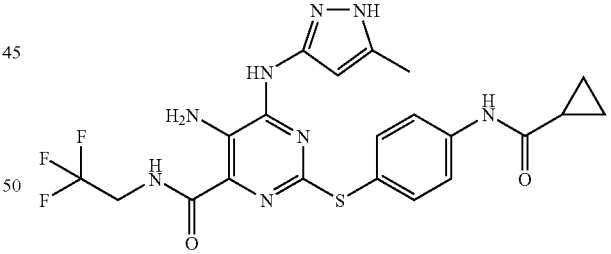

N-(2,2,2-Trifluoroethyl) 2-(4-cyclopropanecarboxamidophenylsulfanyl)-5-amino-6-(5-methylpyrazol-3-ylamino)-4-pyrimidinecarboxamide (Compound 65)

From 2,2,2-trifluoroethanamine and Compound 11 was obtained Example 26: $^1$H NMR (400 MHz, DMSO-$d_6$) δ11.95 (s, 1 H), 10.45 (s, 1 H), 9.51 (s, 1 H), 8.84 (s, 1 H), 7.74 (d, J=7.8 Hz, 2 H), 7.52 (d, J=7.8 Hz, 2 H), 6.89 (s, 2 H), 5.36

(s, 1 H), 4.04 (m, 2H), 1.97 (s, 3 H), 1.81 (m, 1 H), 0.82 (d, J=5.1 Hz, 4 H); MS (electrospray) m/e 507 ($C_{21}H_{21}F_3N_8O_2S$+H).

Example 27

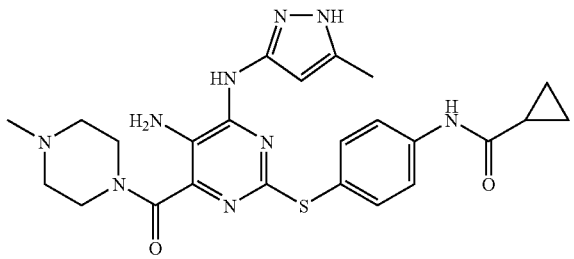

N-(4-Methylpiperazin-1-yl) 2-(4-cyclopropanecarboxamidophenylsulfanyl)-5-amino-6-(5-methylpyrazol-3-ylamino)-4-pyrimidinecarboxamide (Compound 68)

From 1-methylpiperazine and Compound 11 was obtained Example 27: $^1$H NMR (300 MHz, DMSO-$d_6$) δ 10.48 (s, 1 H), 9.54 (s, 1 H), 7.72 (d, J=8.4 Hz, 2 H), 7.5 (d, J=8.4 Hz, 2 H), 5.6 (s, 1 H), 4.82 (s, 2 H), 3.5-3.7 (m, 4 H), 2.6 (s, 3 H), 2.3-2.4 (m, 4 H), 1.97 (s, 3 H), 1.75-1.85 (m, 1 H), 0.78-0.85 (m, 4 H); MS (electrospray) m/e 508 ($C_{24}H_{29}N_9O_2S$+H).

Example 28

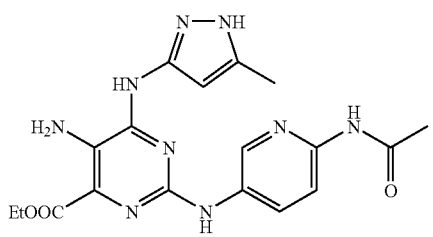

Ethyl 2-(6-acetylamido-3-pyridylamino)-5-amino-6-(5-methylpyrazol-3-ylamino)-4-pyrimidinecarboxylate (Compound 34)

Example 28 was obtained by substituting N-(5-aminopyridin-2-yl)acetamide for 4-cyclopropanecarboxamidothiophenol in the reaction sequence used to prepare Compound 11 in Example 4: $^1$H NMR (400 MHz, DMSO-$d_6$) δ 12.11 (s, 1 H), 10.26 (s, 1 H), 9.34 (s, 1 H), 8.87 (s, 1 H), 8.78 (s, 1 H), 8.23 (d, J=8.4 Hz, 2 H), 7.92 (d, J=8.4 Hz, 2 H), 6.72 (s, 1 H), 6.35 (br s, 2 H), 4.3 (q, J=6.8 Hz, 2 H), 2.21 (s, 3 H), 2.05 (s, 3 H), 1.34 (t, J=6.8 Hz, 3 H); MS (electrospray) m/e 412 ($C_{18}H_{21}N_9O_3$+H).

Example 29

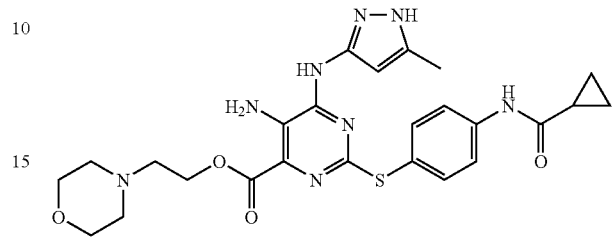

2-Morpholin-4-ylethyl 2-(4-cyclopropanecarboxamidophenylsulfanyl)-5-amino-6-(5-methylpyrazol-3-ylamino)-4-pyrimidinecarboxylate (Compound 18)

To a mixture of Compound 11 (192 mg, 0.42 mmol, 1 equiv) and 2-morpholin-4-ylethanol (4 ml) was added titanium tetraisopropoxide (0.012 mL, 0.04 mmol, 0.1 equiv). The reaction was heated at 100° C. overnight, cooled to rt, treated with aqueous $NaHCO_3$ solution (10 mL), and extracted with EtOAc (3×25 mL). The combined EtOAc layer was dried over $Na_2SO_4$ and concentrated to give a gummy residue. The residue was treated with a small amount of EtOAc/hexane (4 mL, 3:1, v/v) and the resulting precipitate was collected and re-crystallized from EtOAc/petroleum ether to give Example 29 as a white solid (50 mg, 22%): $^1$H NMR (DMSO-$d_6$, 400 MHz) δ 11.95 (s, 1 H), 10.43 (s, 1 H), 9.51 (s, 1 H), 7.72 (d, J=8.2 Hz, 2 H), 7.49 (d, J=8.2 Hz, 2 H), 6.70 (s, 2 H), 5.39 (s, 1 H), 4.36 (t, J=5.8 Hz, 2 H), 3.58 (t, J=4.4 Hz, 4 H), 2.65 (t, J=5.8 Hz, 2 H), 2.47-2.51 (m, 4 H), 1.97 (s, 3 H), 1.82 (m, 1 H), 0.81 (d, J=6.0 Hz, 4 H) MS (electrospray) m/e 539 ($C_{25}H_{30}N_8O_4S$+H).

Example 30

Tetrahydro-2H-pyran-4-yl 2-(4-cyclopropanecarboxamidophenylsulfanyl)-5-amino-6-(5-methylpyrazol-3-ylamino)-4-pyrimidinecarboxylate (Compound 19)

To a solution of Compound 11 (100 mg, 0.23 mmol, 1 equiv) in tetrahydro-2H-pyran-4-ol (1 mL) was added KCN (5 mg, 0.077 mmol, 0.33 equiv). The solution was refluxed overnight. The reaction mixture was cooled to rt and diluted with water. The resulting solid was collected and purified by preparative HPLC to give Example 30 as a white solid (40 mg, 35%): $^1$H NMR (400 MHz, DMSO-$d_6$) δ 11.96 (s, 1 H), 10.42 (s, 1H), 9.54 (s, 1 H), 7.72 (d, J=8.5 Hz, 2 H), 7.51 (d, J=8.5 Hz, 2 H), 6.74 (s, 2 H), 5.44 (s, 1 H), 5.06 (m, 1 H), 3.84-3.87 (m, 2 H), 3.46-3.52 (m, 2 H), 1.99 (s, 3H), 1.92-1.97 (m, 2 H), 1.81 (m, 1 H), 1.66-1.70 (m, 2 H), 0.81 (d, J=6.1 Hz, 4 H); MS (electrospray) m/e 510 ($C_{24}H_{27}N_7O_4S$+H).

Example 31-40 were prepared in the same manner as Examples 29 and 30 by substituting the appropriate alcohol for 2-morpholin-4-ylethanol or tetrahydro-2H-pyran-4-ol, respectively.

Example 31

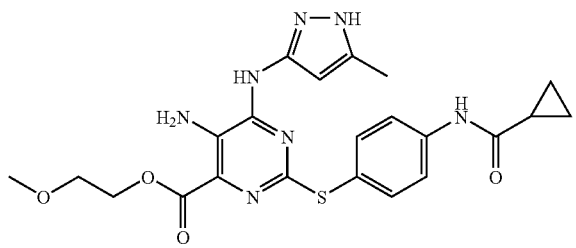

2-Methoxyethyl 2-(4-cyclopropanecarboxamidophenylsulfanyl)-5-amino-6-(5-methylpyrazol-3-ylamino)-4-pyrimidinecarboxylate (Compound 40)

From 2-methoxyethanol and Compound 11 was obtained Example 31: $^1$H NMR (400 MHz, DMSO-$d_6$) δ 11.95 (s, 1 H), 10.43 (s, 1 H), 9.54 (s, 1 H), 7.72 (d, J=7.8 Hz, 2 H), 7.50 (d, J=7.8 Hz, 2 H), 6.73 (s, 2 H), 5.36 (s, 1 H), 4.37 (t, J=4.6 Hz, 2 H), 3.65 (t, J=4.6 Hz, 2 H), 3.26 (s, 3 H), 1.97 (s, 3 H), 1.81-1.84 (m, 1 H), 0.82 (d, J=6.1 Hz, 4 H); MS (electrospray) m/e 484 ($C_{22}H_{25}N_7O_4S$+H).

Example 32

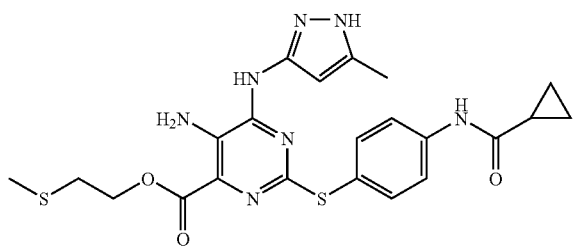

(2-(Methylthio)ethyl 2-(4-cyclopropanecarboxamidophenylsulfanyl)-5-amino-6-(5-methylpyrazol-3-ylamino)-4-pyrimidinecarboxylate (Compound 41)

From 2-(methylthio)ethanol and Compound 11 was obtained Example 32: $^1$H NMR (400 MHz, DMSO-$d_6$) δ 11.95 (s, 1 H), 10.43 (s, 1 H), 9.55 (s, 1 H), 7.72 (d, J=8.5 Hz, 2 H), 7.50 (s, J=8.5 Hz, 2 H), 6.75 (s, 2 H), 5.35 (s, 1 H), 4.40 (t, J=6.8 Hz, 2 H), 2.83 (t, J=6.8 Hz, 2 H), 2.18 (s, 3 H), 1.96 (s, 3 H), 1.80-1.84 (m, 1 H), 0.82 (d, J=6.1 Hz, 4 H); MS (electrospray) m/e 500 ($C_{22}H_{25}N_7O_3S_2$+H).

Example 33

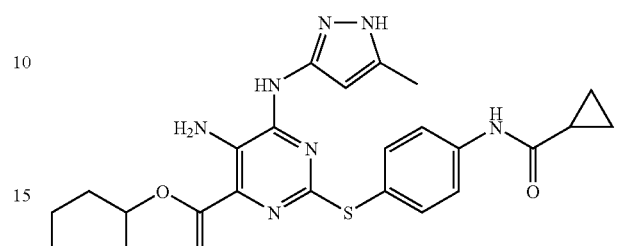

Cyclohexyl 2-(4-cyclopropanecarboxamidophenylsulfanyl)-5-amino-6-(5-methylpyrazol-3-ylamino)-4-pyrimidinecarboxylate (Compound 42)

From cyclohexanol and Compound 11 was obtained Example 33: $^1$H NMR (400 MHz, DMSO-$d_6$) δ 11.96 (s, 1 H), 10.42 (s, 1 H), 9.52 (s, 1 H), 7.72 (d, J=8.6 Hz, 2 H), 7.51 (d, J=8.6 Hz, 2 H), 6.71 (s, 2 H), 5.44 (s, 1 H), 4.86-4.91 (m, 1 H), 1.99 (s, 3 H), 1.87-1.90 (m, 2 H), 1.82 (m, 1 H), 1.71-1.73 (m, 2 H), 1.50-1.53 (m, 3 H), 1.36-1.39 (m, 3 H), 0.81 (d, J=6.0 Hz, 4 H); MS (electrospray) m/e 508 $C_{25}H_{29}N_7O_3S$+H).

Example 34

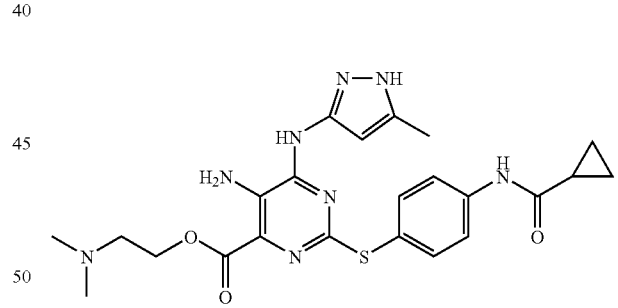

2-Dimethylaminoethyl 2-(4-cyclopropanecarboxamidophenylsulfanyl)-5-amino-6-(5-methylpyrazol-3-ylamino)-4-pyrimidinecarboxylate (Compound 46)

From 2-(dimethylamino)ethanol and Compound 11 was obtained Example 34: $^1$H NMR (400 MHz, DMSO-$d_6$) δ 11.95 (s, 1 H), 10.43 (s, 1 H), 9.53 (s, 1 H), 7.73 (d, J=8.4, 2H), 7.50 (d, J=8.4 Hz, 2 H), 6.72 (s, 2 H), 5.38 (s, 1 H), 4.33 (t, J=5.7 Hz, 2 H), 2.61 (t, J=5.7 Hz, 2 H) 2.24 (s, 6 H), 1.97

(s, 3 H), 1.80 (m, 1 H), 0.81 (d, J=5.9 Hz, 4 H); MS (electrospray) m/e 497 ($C_{23}H_{28}N_8O_3S$+H).

Example 35

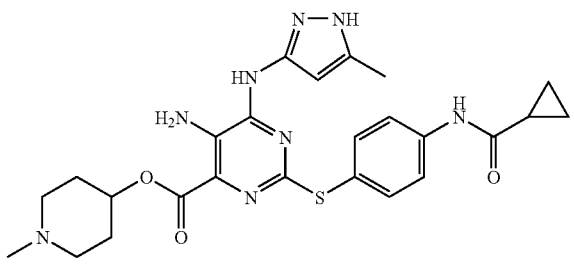

1-Methylpiperidin-4-yl 2-(4-cyclopropanecarboxamidophenylsulfanyl)-5-amino-6-(5-methylpyrazol-3-ylamino)-4-pyrimidinecarboxylate (Compound 47)

From 1-methylpiperidin-4-ol and Compound 11 was obtained Example 35: $^1$H NMR (400 MHz, DMSO-$d_6$) δ11.97 (s, 1 H), 10.43 (s, 1 H), 9.54 (s, 1 H), 7.72 (br s, 2H), 7.52 (br s, 2 H), 6.73 (s, 2 H), 5.43 (s, 1 H), 4.86 (br s, 1 H), 2.69 (br s, 2 H), 2.35 (br s, 5 H), 1.79-2.33 (m, 6 H), 1.26 (br s, 2 H), 0.82 (br s, 4 H); MS (electrospray) m/e 523 ($C_{25}H_{30}N_8O_3S$+H).

Example 36

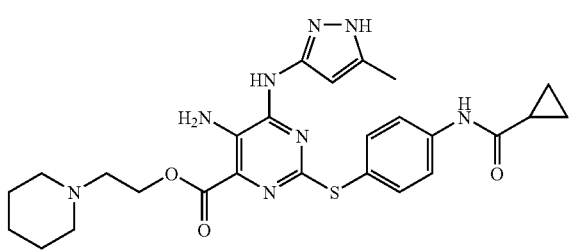

2-Piperidin-1-ylethyl 2-(4-cyclopropanecarboxamidophenylsulfanyl)-5-amino-6-(5-methylpyrazol-3-ylamino)-4-pyrimidinecarboxylate (Compound 48)

From 2-piperidin-1-ylethanol and Compound 11 was obtained Example 36: $^1$H NMR (400 MHz, DMSO-$d_6$) δ10.44 (s, 1 H), 9.57 (br s, 1 H), 7.72 (d, J=8.5 Hz, 2 H), 7.50 (d, J=8.5 Hz, 2 H), 6.68 (s, 2 H), 5.38 (s, 1 H), 4.34 (t, J=5.9 Hz, 2 H), 2.60 (t, J=5.9 Hz, 2 H), 2.42 (br s, 4 H), 1.91 (s, 3 H), 1.82 (m, 1 H), 1.47-1.51 (m, 4 H), 1.39 (br s, 2 H), 0.81 (d, J=6.0 Hz, 4 H); MS (electrospray) m/e 537 ($C_{26}H_{32}N_8O_3S$+H).

Example 37

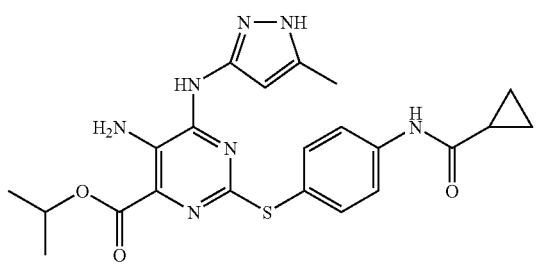

Isopropyl 2-(4-cyclopropanecarboxamidophenylsulfanyl)-5-amino-6-(5-methylpyrazol-3-ylamino)-4-pyrimidinecarboxylate (Compound 49)

From 2-propanol and Compound 11 was obtained Example 37: $^1$H NMR (400 MHz, DMSO-$d_6$) δ11.94 (s, 1 H), 10.43 (s, 1 H), 9.51 (s, 1 H), 7.73 (d, J=8.2 Hz, 2 H), 7.51 (d, J=8.2 Hz, 2 H), 6.73 (s, 2 H), 5.35 (s, 1 H), 5.12 (m, 1 H), 1.96 (s, 3 H), 1.81 (m, 1 H), 1.32 (m, 6 H), 0.81 (br s, 4 H); MS (electrospray) m/e 468 ($C_{22}H_{25}N_7O_3S$+H).

Example 38

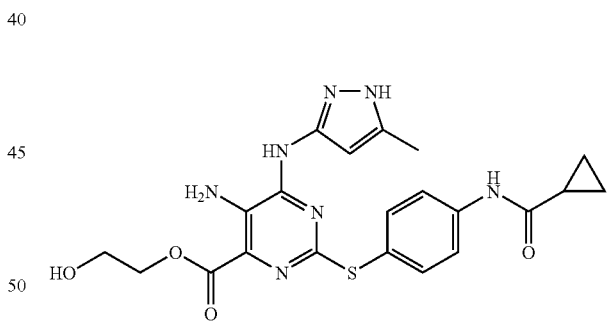

2-Hydroxyethyl 2-(4-cyclopropanecarboxamidophenylsulfanyl)-5-amino-6-(5-methylpyrazol-3-ylamino)-4-pyrimidinecarboxylate (Compound 50)

From ethylene glycol and Compound 11 was obtained Example 38: $^1$H NMR (400 MHz, DMSO-$d_6$) δ11.95 (s, 1 H), 10.44 (s, 1 H), 9.54 (s, 1 H), 7.73 (d, J=8.5 Hz, 2 H), 7.50 (d, J=8.5 Hz, 2 H), 6.71 (s, 2 H), 5.31 (s, 1 H), 4.95 (m, 1 H), 4.27

(t, J=5.0 Hz, 2H), 3.71 (t, J=5.0 Hz, 2 H), 1.96 (s, 3 H), 1.82 (m, 1 H), 0.81 (d, J=5.9 Hz, 4 H); MS (electrospray) m/e 470 ($C_{21}H_{23}N_7O_4S$+H).

Example 39

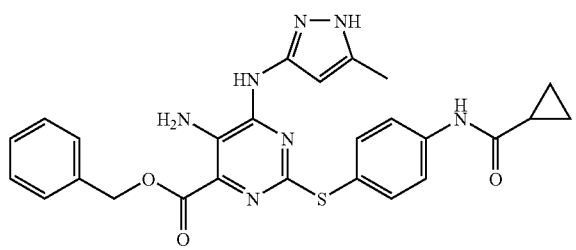

Benzyl 2-(4-cyclopropanecarboxamidophenylsulfanyl)-5-amino-6-(5-methylpyrazol-3-ylamino)-4-pyrimidinecarboxylate (Compound 66)

From benzyl alcohol and Compound 11 was obtained Example 39: $^1$H NMR (300 MHz, DMSO-$d_6$) δ11.92 (s, 1 H), 10.41 (s, 1 H), 9.54 (s, 1 H), 7.69 (d, J=8.4 Hz, 2 H), 7.3-7.5 (m, 7 H), 6.76 (s, 2 H), 5.38 (s, 1 H), 5.3 (s, 2 H), 1.97 (s, 3 H), 1.75-1.85 (m, 1H), 0.78-0.85 (m, 4 H); MS (electrospray) m/e 516 ($C_{26}H_{25}N_7O_3S$+H).

Example 40

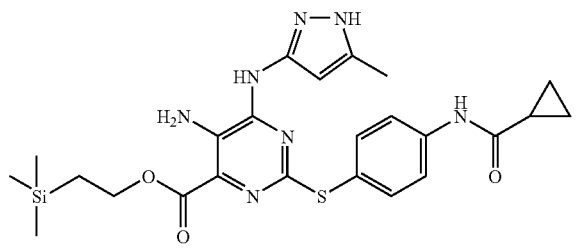

2-(Trimethylsilyl)ethyl) 2-(4-cyclopropanecarboxamidophenylsulfanyl)-5-amino-6-(5-methylpyrazol-3-ylamino)-4-pyrimidinecarboxylate (Compound 67)

From 2-(trimethylsilyl)ethanol and Compound 11 was obtained Example 40: $^1$H NMR (300 MHz, DMSO-$d_6$) δ11.92 (s, 1H), 10.41 (s, 1H), 9.54 (s, 1H), 7.68 (d, J=8.4 Hz, 2H), 7.5 (d, J=8.4 Hz, 2H), 6.75 (s, 2 H), 5.38 (s, 1 H), 4.3 (t, J=7.8 Hz, 2 H), 1.97 (s, 3 H), 1.75-1.85 (m, 1 H), 1.1 (t, J=7.8 Hz, 2 H), 0.78-0.85 (m, 4 H), 0.07 (s, 9 H); MS (electrospray) m/e 526 ($C_{24}H_{31}N_7O_3SSi$+H).

Example 41

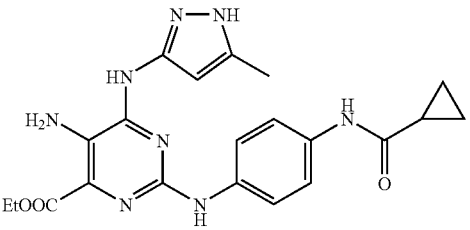

Ethyl 2-({4-[(cyclopropylcarbonyl)amino]phenyl}amino)-5-amino-6-(5-methylpyrazol-3-ylamino)-4-pyrimidinecarboxylate (Compound 36)

Example 41 was obtained by substituting N-(4-aminophenyl)cyclopropanecarboxamide for 4-cyclopropanecarboxamido-thiophenol in the reaction sequence used to prepare Compound 11 in Example 4: $^1$H NMR (400 MHz, DMSO-$d_6$) δ 11.20 (s, 1 H), 10.32 (s, 1 H), 9.87 (s, 1 H), 7.62 (d, J=8.2 Hz, 2 H), 7.40 (br s, 2 H), 6.96 (br s, 2 H), 6.18 (s, 1 H), 4.42 (q, J=7.0 Hz, 2 H), 2.18 (s, 3 H), 1.80 (m, 1 H), 1.39 (t, J=7.0 Hz, 3 H), 0.80 (d, J=4.6 Hz, 4 H); MS (electrospray) m/e 437 ($C_{21}H_{24}N_8O_3$+H).

BIOLOGICAL EXAMPLES

A. PanVera Aurora Kinase Assay

Compounds 7-14 above were tested for their potency against recombinant Aurora A (Upstate, Lake Placid, N.Y.) using the PanVera Z'-Lyte kinase assay kit—Ser/Thr 1 peptide (Invitrogen, Carlsbad, Calif.). Assays were carried out in kinase assay buffer (50 mM HEPES, pH 7.5, 10 mM $MgCl_2$, 5 mM EGTA, 0.05% Brij-35, 2 mM DTT). Test compounds were initially dissolved in DMSO at 100× the highest tested concentration, then serially diluted to 4× test concentrations in kinase assay buffer. Next, Aurora A (final concentration 200-500 ng/mL), Z'-Lyte Ser/Thr 1 peptide (final concentration 2 μM) and ATP (final concentration 10 μM) were added according to the manufacturer's instructions. Assays were carried out in half-area 96-well white polystyrene assay plates (Corning, Corning, N.Y.) in a final volume of 20 μL. The reaction was allowed to proceed for 1 h at room temperature in the dark, at which point the development reagent and stop reagent were added according to the manufacturer's instructions. Coumarin (Ex. 400 nm, Em. 465 nm) and fluorescein (Ex. 400 nm, Em. 565 nm) fluorescence values were measured on a SpectraFluor Plus plate reader (Tecan, Durham, N.C.). The emission ratio (coumarin/fluorescein) was determined and used to calculate the percent phosphorylation for each well. Wells containing substrate but no kinase and wells containing a phosphopeptide control were used to set 0% and 100% phosphorylation values, respectively. Typically 20-40% of the substrate was phosphorylated in wells without inhibitor. Dose-response curves of relative Aurora A activity vs. inhibitor concentration were plotted with Grafit (Erithacus Software, Horley, Surrey, UK) and used to calculate $IC_{50}$ values.

B. Aurora B (Aurora 1) Inhibition Assay

Assays for Auorora B kinase inhibition were carried out similarly to those for Aurora A kinase (see above) with the following modifications. Aurora B kinase (San Diego, Calif.) was used as the enzyme at a concentration of 2.5 μg/mL. The ATP concentration was 50 μM, and the kinase reaction was allowed to proceed for 16 h. Sodium orthovanadate (20 μM) was added to the buffer to inhibit contaminating phosphatases.

At a compound concentration of 100 μM in this assay, both Compound 11 and Compound 52 inhibited the Aurora B enzyme by 100 percent.

C. Aurora Kinase Whole Cell Cytotoxicity

Assay: Sulforhodamine B

Reference: Developmental Therapeutics Program NCI/NIH
http://dtp.nci.nih.gov/brancehes/btb/ivclsp.html Human tumour-derived cell lines, HCT116 or MCF7 (ATCC) were plated in a 96 well plate in DMEM containing 10% fetal bovine serum and 2 mM L-glutamine at a density of 500 HCT116 cells or 1,000 MCF7 cells per well and incubated at 37° C., 5% $CO_2$, for 24 hours prior to the addition of experimental compounds. Compounds were added using the dilution series indicated to duplicate plates and the cells were incubated in media plus compound for 96 hours. An additional plate was fixed in 10% TCA at the time of the addition of compound to provide a measurement of the cell population at time zero, the time of drug addition. Following the 96 hour incubation, cells were fixed in situ by gently aspirating off the culture media and then adding 50 ul of ice cold 10% TCA per well and incubation at 4° C. for 60 minutes. The plates were washed with tap water five times and allowed to air dry for 5 minute. 50 ul of a 0.4% (w/v) Sulforhodamine B solution in 1% (v/v) acetic acid was added per well and the cells were incubated for 30 minutes at room temperature. Following staining, plates were washed four times with 1% acetic acid to remove any unbound dye and then allowed to air dry for 5 minutes. The stain was solubilized with 100 ul of 10 mM Tris pH 10.5 per well and placed on an orbital rotator for 5 minutes. The absorbance was read at 570 nm. Percentage growth was calculated using the absorbance readings from the time zero plate (Tz) and the dilution series plate (C) which included a column of cells grown in media without compound as a control (C) using the formulas:

[(Ti−Tz)/(*C−Tz*)]×100 for concentrations for which Ti>/=Tz

[(Ti−Tz)/Tz]×100 for concentrations for which Ti<Tz.

Three dose response parameters were calculated for each experimental agent. Growth inhibition of 50% (GI50) was calculated from [(Ti−Tz)/(C−Tz)]×100=50, which was the drug concentration resulting in a 50% reduction in the net protein increase (as measured by SRB staining) in control cells during the drug incubation. The drug concentration resulting in total growth inhibition (TGI) was calculated from Ti=Tz. The LC50 (concentration of drug resulting in a 50% reduction in the measured protein at the end of the drug treatment as compared to that at the beginning) indicating a net loss of cells following treatment ws calculated from [(Ti−Tz)/Tz]×100=−50. Values are calculated for each of these three parameters if the level of activity was reached; however, if the effect was not reached or was exceeded, the value for that parameter is expressed as greater or less than the maximum or minimum concentration tested.

The results of these assays are set forth in the Table II below wherein the $IC_{50}$ or $GI_{50}$ values are grouped as follows:

Group A: $IC_{50}$ or $GI_{50}$ less than 0.1 μM;
Group B: $IC_{50}$ or $GI_{50}$ between 0.1-1.0 μM; and
Group C: $IC_{50}$ or $GI_{50}$ between 1-10 μM;

TABLE II

| Compound Number | $IC_{50}$ Aurora A | $GI_{50}$ HCT 116 Cells |
|---|---|---|
| 7 | A | B |
| 8 | A | |
| 9 | A | |
| 11 | A | B |
| 12 | A | C |
| 13 | A | |
| 14 | A | |
| 17 | A | B |
| 18 | A | C |
| 19 | A | B |
| 34 | B | |
| 36 | A | C |
| 40 | A | B |
| 41 | A | B |
| 42 | A | B |
| 43 | A | B |
| 44 | A | C |
| 45 | A | C |
| 46 | A | B |
| 47 | A | B |
| 48 | A | C |
| 49 | A | B |
| 50 | A | C |
| 51 | A | C |
| 52 | A | B |
| 53 | A | B |
| 54 | A | B |
| 55 | A | B |
| 56 | A | B |
| 57 | B | C |
| 58 | A | C |
| 59 | A | C |
| 60 | B | |
| 61 | A | B |
| 62 | B | C |
| 63 | A | B |
| 64 | A | B |
| 65 | A | B |
| 66 | A | B |
| 67 | B | C |
| 68 | C | C |

What is claimed is:

1. A compound of formula Ia or Ib:

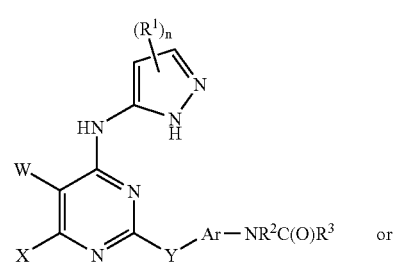

-continued

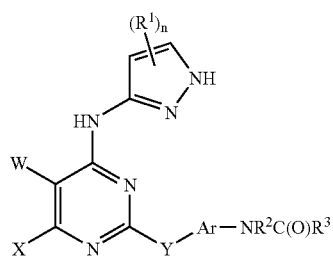

wherein Ar is $C_6$-$C_{14}$;

W is amino;

X is carboxyl esters or aminoacyl;

Y is selected from the group consisting of oxygen, sulfur, —S(O)—, —S(O)$_2$—, and —NH—;

each $R^1$ is $C_1$-$C_{10}$ alkyl;

$R^2$ is hydrogen;

$R^3$ is $C_3$-$C_{10}$ cycloalkyl; and n is 1;

or pharmaceutically acceptable salts thereof.

2. A compound according to claim 1, wherein Y is selected from the group consisting of —S—, —S(O)— and —S(O)$_2$—.

3. A compound of claim 1 having formula IIIa or IIIb:

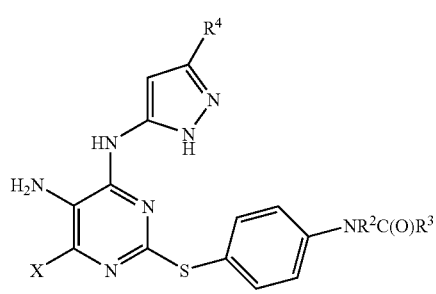

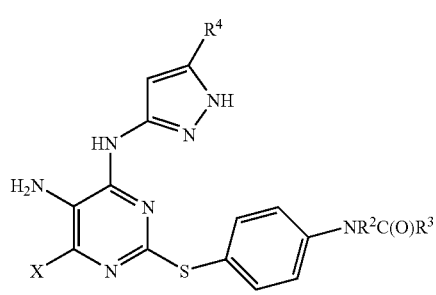

wherein:

X is carboxyl esters or aminoacyl;

$R^2$ is hydrogen;

$R^3$ is $C_3$-$C_{10}$ cycloalkyl; and $R^4$ is $C_1$-$C_{10}$ alkyl;

or pharmaceutically acceptable salts thereof.

4. A compound according to claim 3, wherein $R^4$ is methyl.

5. A compound of formula IIa or IIb:

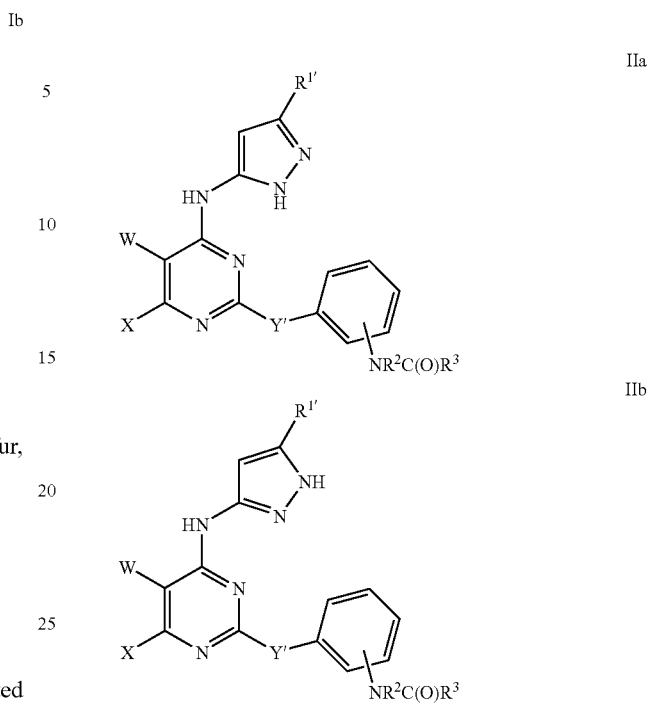

wherein:

W is amino;

X is carboxyl esters or aminoacyl;

Y' is selected from the group consisting of sulfur, —S(O)—, and —S(O)$_2$—;

$R^{1'}$ is hydrogen, acylamino, $C_1$-$C_{10}$ alkyl;

$R^2$ is hydrogen; and $R^3$ is $C_3$-$C_{10}$ cycloalkyl;

or pharmaceutically acceptable salts thereof.

6. The compound according to claim 1, wherein X is selected from the group consisting of

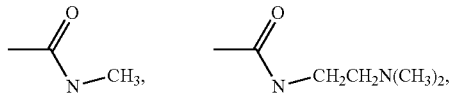

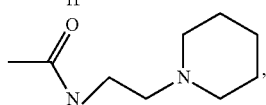

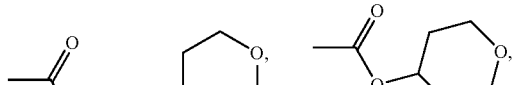

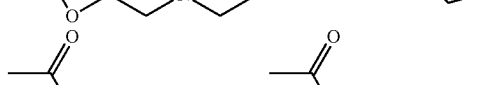

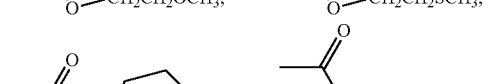

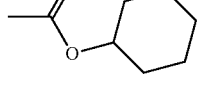

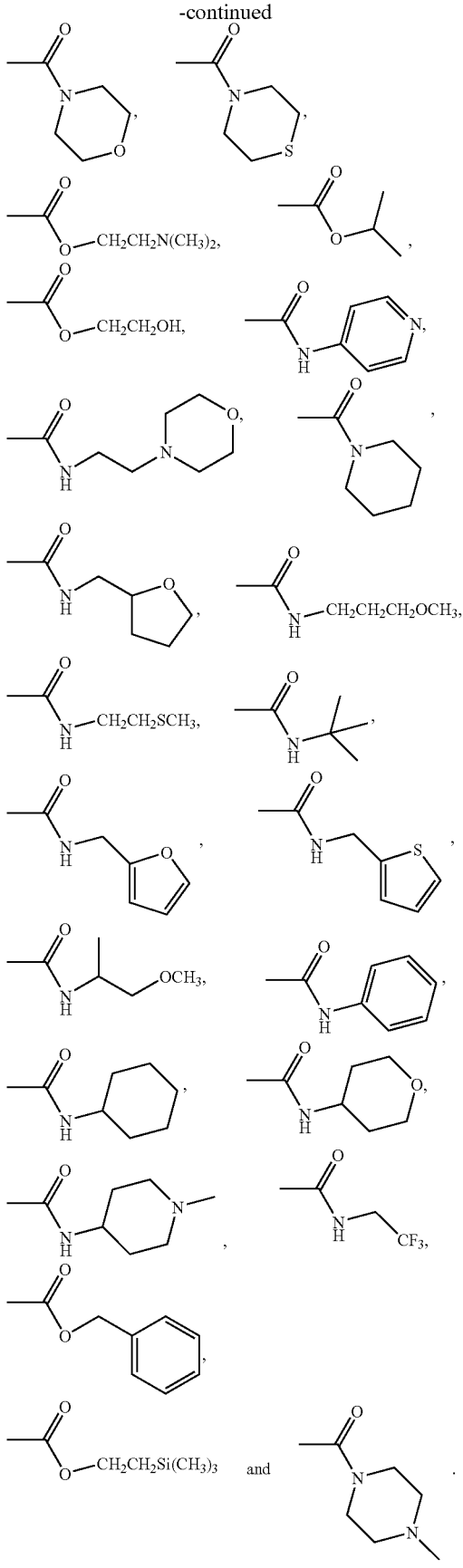

7. A compound according to any one of claim 1, 5 or 3, wherein $R^3$ is cyclopropyl.

8. A compound according to claim 7, wherein $R^{1'}$ is methyl.

9. A compound selected from ethyl 2-(4-cyclopropanecarboxamidophenylsulfanyl)-5-amino-6-(5-methylpyrazol-3-ylamino)-4-pyrimidinecarboxylate;

N-[2-(N,N-dimethylamino)ethyl]-2-(4-cyclopropanecarboxamidophenylsulfanyl)-5-amino-6-(5-methylpyrazol-3-ylamino)-4-pyrimidinecarboxamide;

N-methyl-2-(4-cyclopropanecarboxamidophenylsulfanyl)-5-amino-6-(5-methylpyrazol-3-ylamino)-4-pyrimidinecarboxamide;

ethyl 2-(4-cyclopropanecarboxamidophenylsulfonyl)-5-amino-6-(5-methylpyrazol-3-ylamino)-4-pyrimidinecarboxylate;

ethyl 2-(4-cyclopropanecarboxamidophenylsulfinyl)-5-amino-6-(5-methylpyrazol-3-ylamino)-4-pyrimidinecarboxylate;

2-(4-cyclopropanecarboxamidophenylsulfanyl)-5-amino-6-(5-methylpyrazol-3-ylamino)-4-pyrimidinecarboxylic acid;

methyl 2-(4-cyclopropanecarboxamidophenylsulfanyl)-5-amino-6-(5-methylpyrazol-3-ylamino)-4-pyrimidinecarboxylate;

ethyl 2-(6-acetylamido-3-pyridylamino)-5-amino-6-(5-methylpyrazol-3-ylamino)-4-pyrimidinecarboxylate;

N-(2-piperidin-l-ylethyl)-2-(4-cyclopropanecarboxamidophenylsulfanyl)-5-amino-6-(5-methylpyrazol-3-ylamino)-4-pyrimidinecarboxamide;

N-(2-methoxyethyl)-2-(4-cyclopropanecarboxamidophenylsulfanyl)-5-amino-6-(5-methylpyrazol-3-ylamino)-4-pyrimidinecarboxamide;

morpholin-4-yl 2-(4-cyclopropanecarboxamidophenylsulfanyl)-5-amino-6-(5-methylpyrazol-3-ylamino)-4-pyrimidinecarboxamide;

thiomorpholin-4-yl 2-(4-cyclopropanecarboxamidophenylsulfanyl)-5-amino-6-(5-methylpyrazol-3-ylamino)-4-pyrimidinecarboxamide;

N-pyridin-4-yl-2-(4-cyclopropanecarboxamidophenylsulfanyl)-5-amino-6-(5-methylpyrazol-3-ylamino)-4-pyrimidinecarboxamide;

N-(2-morpholin-4-ylethyl)-2-(4-cyclopropanecarboxamidophenylsulfanyl)-5-amino-6-(5-methylpyrazol-3-ylamino)-4-pyrimidinecarboxamide;

piperidin-1-yl 2-(4-cyclopropanecarboxamidophenylsulfanyl)-5-amino-6-(5-methylpyrazol-3-ylamino)-4-pyrimidinecarboxamide;

N-(tetrahydrofuran-2-ylmethyl)-2-(4-cyclopropanecarboxamidophenylsulfanyl)-5-amino-6-(5-methylpyrazol-3-ylamino)-4-pyrimidinecarboxamide;

N-(3-methoxypropyl)-2-(4-cyclopropanecarboxamidophenylsulfanyl)-5-amino-6-(5-methylpyrazol-3-ylamino)-4-pyrimidinecarboxamide;

N-(2-methylthioethyl)-2-(4-cyclopropanecarboxamidophenylsulfanyl)-5-amino-6-(5-methylpyrazol-3-ylamino)-4-pyrimidinecarboxamide;

N-(tert-butyl) 2-(4-cyclopropanecarboxamidophenylsulfanyl)-5-amino-6-(5-methylpyrazol-3-ylamino)-4-pyrimidinecarboxamide;

N-(2-furylmethyl)-2-(4-cyclopropanecarboxamidophenylsulfanyl)-5-amino-6-(5-methylpyrazol-3-ylamino)-4-pyrimidinecarboxamide;

N-(2-thien-2-ylmethyl)-2-(4-cyclopropanecarboxamidophenylsulfanyl)-5-amino-6-(5-methylpyrazol-3-ylamino)-4-pyrimidinecarboxamide;

N-phenyl-2-(4-cyclopropanecarboxamidophenylsulfanyl)-5-amino-6-(5-methylpyrazol-3-ylamino)-4-pyrimidinecarboxamide;

N-(2-methoxy-1-methylethyl)-2-(4-cyclopropanecarboxamidophenylsulfanyl)-5-amino-6-(5-methylpyrazol-3-ylamino)-4-pyrimidinecarboxamide;

N-cyclohexyl-2-(4-cyclopropanecarboxamidophenylsulfanyl)-5-amino-6-(5-methylpyrazol-3-ylamino)-4-pyrimidinecarboxamide;

N-tetrahydro-2H-pyran-4-yl-2-(4-cyclopropanecarboxamidophenylsulfanyl)-5-amino-6-(5-methylpyrazol-3-ylamino)-4-pyrimidinecarboxamide;

N-(1-methylpiperidin-4-yl)-2-(4-cyclopropanecarboxamidophenylsulfanyl)-5-amino-6-(5-methylpyrazol-3-ylamino)-4-pyrimidinecarboxamide;

N-(2,2,2-trifluoroethyl)-2-(4-cyclopropanecarboxamidophenylsulfanyl)-5-amino-6-(5-methylpyrazol-3-ylamino)-4-pyrimidinecarboxamide;

N-(4-methylpiperazin-1-yl)-2-(4-cyclopropanecarboxamidophenylsulfanyl)-5-amino-6-(5-methylpyrazol-3-ylamino)-4-pyrimidinecarboxamide;

2-morpholin-4-ylethyl 2-(4-cyclopropanecarboxamidophenylsulfanyl)-5-amino-6-(5-methylpyrazol-3-ylamino)-4-pyrimidinecarboxylate;

tetrahydro-2H-pyran-4-yl 2-(4-cyclopropanecarboxamidophenylsulfanyl)-5-amino-6-(5-methylpyrazol-3-ylamino)-4-pyrimidinecarboxylate;

2-methoxyethyl 2-(4-cyclopropanecarboxamidophenylsulfanyl)-5-amino-6-(5-methylpyrazol-3-ylamino)-4-pyrimidinecarboxylate;

2-(methylthio)ethyl 2-(4-cyclopropanecarboxamidophenylsulfanyl)-5-amino-6-(5-methylpyrazol-3-ylamino)-4-pyrimidinecarboxylate;

cyclohexyl 2-(4-cyclopropanecarboxamidophenylsulfanyl)-5-amino-6-(5-methylpyrazol-3-ylamino)-4-pyrimidinecarboxylate;

2-dimethylaminoethyl 2-(4-cyclopropanecarboxamidophenylsulfanyl)-5-amino-6-(5-methylpyrazol-3-ylamino)-4-pyrimidinecarboxylate;

1-methylpiperidin-4-yl 2-(4-cyclopropanecarboxamidophenylsulfanyl)-5-amino-6-(5-methylpyrazol-3-ylamino)-4-pyrimidinecarboxylate;

2-piperidin-1-ylethyl 2-(4-cyclopropanecarboxamidophenylsulfanyl)-5-amino-6-(5-methylpyrazol-3-ylamino)-4-pyrimidinecarboxylate;

isopropyl 2-(4-cyclopropanecarboxamidophenylsulfanyl)-5-amino-6-(5-methylpyrazol-3-ylamino)-4-pyrimidinecarboxylate;

2-hydroxyethyl 2-(4-cyclopropanecarboxamidophenylsulfanyl)-5-amino-6-(5-methylpyrazol-3-ylamino)-4-pyrimidinecarboxylate;

benzyl 2-(4-cyclopropanecarboxamidophenylsulfanyl)-5-amino-6-(5-methylpyrazol-3-ylamino)-4-pyrimidinecarboxylate;

2-(trimethylsilyl)ethyl) 2-(4-cyclopropanecarboxamidophenylsulfanyl)-5-amino-6-(5-methylpyrazol-3-ylamino)-4-pyrimidinecarboxylate;

ethyl 2-({4-[(cyclopropylcarbonyl)amino]phenyl}amino)-5-amino-6-(5-methylpyrazol-3-ylamino)-4-pyrimidinecarboxylate;

or pharmaceutically acceptable salts or tautomers thereof.

10. A pharmaceutical composition comprising a pharmaceutically acceptable diluent and one or more compounds as defined in any one of claims 1, 7, 3, 6, or 9.

11. A method for treating colorectal cancer in a patient which method comprises administering to said patient a compound or mixture of compounds according to any one of claims 1, 7, 3, or 6.

12. A method for treating colorectal cancer in a patient which method comprises administering to said patient a compound or mixture of compounds according to claim 9.

* * * * *

UNITED STATES PATENT AND TRADEMARK OFFICE
CERTIFICATE OF CORRECTION

PATENT NO. : 8,153,630 B2
APPLICATION NO. : 11/667205
DATED : April 10, 2012
INVENTOR(S) : Xiao-Yi Xiao et al.

Page 1 of 2

It is certified that error appears in the above-identified patent and that said Letters Patent is hereby corrected as shown below:

Column 4
Line 18, "alkyl;" should read -- alkyl, --

Column 7
Line 2, "may the same" should read -- may be the same --
Line 14, "moeity" should read -- moiety --
Line 59, "interfereing" should read -- interfering --

Column 8
Line 6 to line 7, "In particular" should read -- In a particular --

Column 34
Line 4, "caboxamidothiophenol" should read -- carboxamidothiophenol --

Column 36
Line 50 to line 51, "available Aldrich" should read
            -- available from Aldrich --

Column 39
Line 25, "face masks tent" should read -- face tent mask --

Column 40
Line 64, "starch, an magnesium" should read -- starch and magnesium --

Column 43
Line 21, "1-(3dimethylamino-propyl)-3-ethylcarbodiimide" should read
       -- 1-(3-dimethylamino-propyl)-3-ethylcarbodiimide --

Signed and Sealed this
Thirty-first Day of July, 2012

David J. Kappos
*Director of the United States Patent and Trademark Office*

CERTIFICATE OF CORRECTION (continued)
U.S. Pat. No. 8,153,630 B2

Column 67
Line 2, "Auorora" should read -- Aurora --
Line 19, "http://dtp.nci.nih.gov/brancehes/btb/ivclsp.html" should read
  -- http://dtp.nci.nih.gov/branches/btb/ivclsp.html --
Line 35, "minute" should read -- minutes --
Line 35, "50 ul" should read -- 50 µl --
Line 40, "100 ul" should read -- 100 µl --

Column 70
Line 35, claim 5 "$R^{1'}$ is hydrogen, acylamino, $C_1$-$C_{10}$ alkyl" should read
  -- $R^{1'}$ is hydrogen, acylamino, or $C_1$-$C_{10}$ alkyl --